(12) United States Patent
Takagaki et al.

(10) Patent No.: US 6,242,425 B1
(45) Date of Patent: Jun. 5, 2001

(54) QUINOLINONE GLYCOSIDE, PRODUCTION PROCESS, AND ANTI-ALLERGIC AGENT

(75) Inventors: Hidetsugu Takagaki; Shigenori Nakanishi; Nobuyuki Kimura, all of Sakura; Shinobu Yamaguchi, Tokyo; Yasuo Aoki, Yotsukaido, all of (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 0 days.

(21) Appl. No.: 09/231,492

(22) Filed: Jan. 14, 1999

(30) Foreign Application Priority Data

Jan. 19, 1998 (JP) .................................................. 10-007462

(51) Int. Cl.$^7$ .......................... A01N 43/04; A61K 31/70; A61K 31/74
(52) U.S. Cl. ................. 514/25; 514/27; 514/311; 514/312; 536/4.1; 536/8; 424/78.05
(58) Field of Search ................................ 514/25, 312, 27; 536/4.1, 8; 424/78.05

(56) References Cited

U.S. PATENT DOCUMENTS 5,525,595 * 6/1996 Takagaki et al. ....................... 514/27
5,580,552 * 12/1996 Takagaki et al. .................. 424/78.05

FOREIGN PATENT DOCUMENTS

| 0 000 153 | 1/1979 | (EP) . |
| 0 646 591 | 4/1995 | (EP) . |
| 0 684 255 | 11/1995 | (EP) . |
| 0 785 190 | 7/1997 | (EP) . |

OTHER PUBLICATIONS

N. Matsui et al., Holzforschung, vol. 48, No. 3, 1994, pp. 215–221, XP002104233.
N. Terashima et al., Holzforschung, vol. 50, No. 2, 1996, pp. 151–155 XP002104234.

\* cited by examiner

Primary Examiner—James O. Wilson
Assistant Examiner—Howard Owens
(74) Attorney, Agent, or Firm—Armstrong, Westerman, Hattori, McLeland & Naughton, LLP

(57) ABSTRACT

An object is to provide: novel quinolinone glycosides which are useful as medicines; processes for producing the quinolinone glycosides; intermediates for synthesis; and medicines, and particularly anti-allergic agents, which comprise the quinolinone glycoside as an active ingredient. The object is achieved by: a quinolinone glycoside or a physiologically acceptable salt thereof; processes for producing this quinolinone glycosides; intermediates for synthesis; and medicines, and particularly anti-allergic agents, which comprise the quinolinone glycoside as an active ingredient; the quinolinone glycoside being expressed by general formula (I):

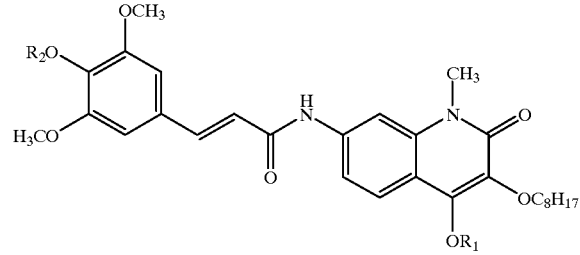

(wherein, in the formula, each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which a hydroxyl group in the glycosyl group is unprotected or protected with an acyl group having a carbon number of 2 to 7 or a benzyl group).

24 Claims, No Drawings

QUINOLINONE GLYCOSIDE, PRODUCTION PROCESS, AND ANTI-ALLERGIC AGENT

BACKGROUND OF THE INVENTION

1. Field of the Invention

The present invention relates to glycosides of quinolinone derivatives or physiologically acceptable salts of such glycosides; processes for producing them; and medicines, and in particular anti-allergic agents, comprising one of them as an active ingredient.

More specifically, the present invention relates to: glycosides represented by general formula (I), in which the glycosidic linkage is formed at a hydroxyl group of 7-(3,5-dimethoxy-4-hydroxycinnamoyl)amino-4-hydroxy-1-methyl-3-octyloxy-2(1H)-quinolinone, represented by general formula (VI), which is the aglycone moiety of the glycosides represented by general formula (I), and physiologically acceptable salts of such glycosides; glycosides represented by general formula (II) or (III), in which the glycosidic linkage is formed at a hydroxyl group portion of a quinolinone derivative, and physiologically acceptable salts of such glycosides; and processes for producing glycosides represented by general formulae (I), (II), (III) and (V). Glycosides represented by general formula (I) are useful as medicines, and particularly as agents for treating or alleviating allergic diseases.

This application is based on Patent Application No. Hei 10-007462 filed in Japan, the content of which is incorporated herein by reference.

2. Background Art

Japanese Patent Application, First Publication (Kokai), No. Hei 9-255659, which was filed by the present inventors, discloses that quinolinone derivative (VI), which is an aglycone moiety of a glycoside expressed by general formula (I) to which the present invention relates, or its physiologically acceptable salt is useful as an agent for treating or alleviating allergic diseases. However, no process for producing a quinolinone glycoside, in which the glycosidic linkage is formed at a hydroxyl group in the quinolinone derivative, and no use of such a quinolinone glycoside have been known. Moreover, the quinolinone glycoside expressed by general formula (II) or (III), which is an important intermediate produced when synthesizing a quinolinone glycoside to which the present invention relates and which is expressed by general formula (I), has also been hitherto unknown.

SUMMARY OF THE INVENTION

An object of the present invention is to provide: novel quinolinone glycosides which are useful as medicines; processes for producing the quinolinone glycosides; intermediates for synthesis; and medicines, and particularly anti-allergic agents, which comprise the quinolinone glycoside as an active ingredient.

The present inventors carried out diligent research in order to achieve the above object, and as a result, by synthesizing various glycosides in which the glycosidic linkage is formed at a hydroxyl group of a quinolinone derivative according to Japanese Patent Application, First Publication (Kokai), No. Hei 9-255659, and by examining the pharmacological action of each of them, the present inventors found such glycosides useful as medicines, and particularly as anti-allergic agents, and achieved the present invention.

That is, the present invention includes:

(1) a quinolinone glycoside or a physiologically acceptable salt thereof, expressed by general formula (I):

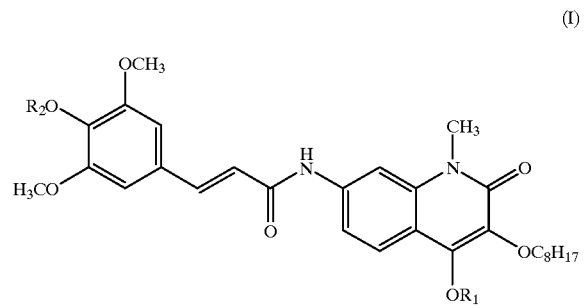

(I)

(wherein, each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which a hydroxyl group is unprotected or protected with an acyl group having a carbon number of 2 to 7 or a benzyl group);

(2) a quinolinone glycoside or a physiologically acceptable salt thereof according to (1), wherein each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which no hydroxyl group is protected;

(3) a quinolinone glycoside or a physiologically acceptable salt thereof according to (1), wherein each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which a hydroxyl group is protected with an acyl group having a carbon number of 2 to 7 or a benzyl group;

(4) a quinolinone glycoside or a physiologically acceptable salt thereof according to (2), wherein each of $R_1$ and $R_2$ is a hydrogen atom or a glucuronyl group in which no hydroxyl group is protected;

(5) a quinolinone glycoside or a physiologically acceptable salt thereof according to (2), wherein each of $R_1$ and $R_2$ is a hydrogen atom or a glucosyl group in which no hydroxyl group is protected;

(6) a quinolinone glycoside or a physiologically acceptable salt thereof according to (2), wherein each of $R_1$ and $R_2$ is a hydrogen atom or a galactosyl group in which no hydroxyl group is protected;

(7) a quinolinone glycoside or a physiologically acceptable salt thereof according to (2), wherein each of $R_1$ and $R_2$ is a hydrogen atom or a mannosyl group in which no hydroxyl group is protected;

(8) a quinolinone glycoside or a physiologically acceptable salt thereof according to (4), wherein each of $R_1$ and $R_2$ is a glucuronyl group in which no hydroxyl group is protected;

(9) a quinolinone glycoside or a physiologically acceptable salt thereof according to (4), wherein $R_1$ is a hydrogen atom, and $R_2$ is a glucuronyl group in which no hydroxyl group is protected;

(10) a quinolinone glycoside or a physiologically acceptable salt thereof according to (4), wherein $R_1$ is a glucuronyl group in which no hydroxyl group is protected, and $R_2$ is a hydrogen atom;

(11) a medicine comprising, as an active ingredient, a quinolinone glycoside or a physiologically acceptable salt thereof as in any one of (2) and (4) to (10);
(12) an anti-allergic agent comprising, as an active ingredient, a quinolinone glycoside or a physiologically acceptable salt thereof as in any one of (2) and (4) to (10);
(13) a quinolinone glycoside or a physiologically acceptable salt thereof, expressed by general formula (II):

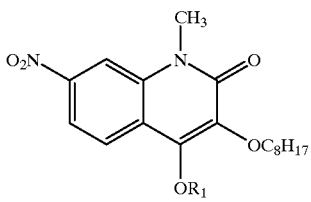

(II)

(wherein $R_1$ is a glycosyl group selected from the group consisting of a glucuronyl group, a glucosyl group, a galactosyl group and a mannosyl group, in which a hydroxyl group is unprotected or protected with an acyl group having a carbon number of 2 to 7 or a benzyl group);
(14) a quinolinone glycoside or a physiologically acceptable salt thereof, expressed by general formula (III):

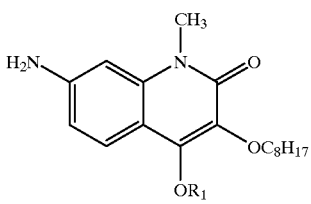

(III)

(wherein $R_1$ is a glycosyl group selected from the group consisting of a glucuronyl group, a glucosyl group, a galactosyl group and a mannosyl group, in which a hydroxyl group is unprotected or protected with an acyl group having a carbon number of 2 to 7 or a benzyl group);
(15) a quinolinone glycoside or a physiologically acceptable salt thereof according to (13), wherein $R_1$ is a glucuronyl group in which a hydroxyl group is protected or unprotected;
(16) a quinolinone glycoside or a physiologically acceptable salt thereof according to (14), wherein $R_1$ is a glucuronyl group in which a hydroxyl group is protected or unprotected;
(17) a process for producing a quinolinone glycoside expressed by general formula (II):

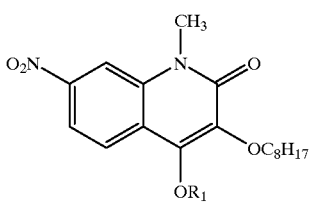

(II)

(wherein $R_1$ is a glycosyl group selected from the group consisting of a glucuronyl group, a glucosyl group, a galactosyl group and a mannosyl group, in which a hydroxyl group is unprotected or protected with an acyl group having a carbon number of 2 to 7 or a benzyl group),
comprising the steps of:
reacting a quinolinone derivative expressed by general formula (IV):

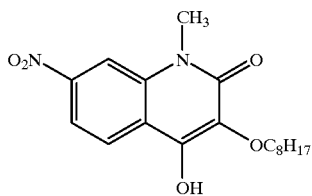

(IV)

with a basic substance; and
then conducting a glycosylation reaction with a glycosyl halide, which is obtained by substituting a hydrogen atom at 1-position of a hexose, selected from the group consisting of, glucuronic acid, glucose, galactose and mannose, by a halogen atom, and in which a hydroxyl group is protected with an acyl group having a carbon number of 2 to 7 or a benzyl group;
(18) a process for producing a quinolinone glycoside according to (17), wherein the basic substance is at least one selected from the group consisting of alkaline metal hydrides, alkaline earth metal hydrides and amines;
(19) a process for producing a quinolinone glycoside expressed by general formula (III):

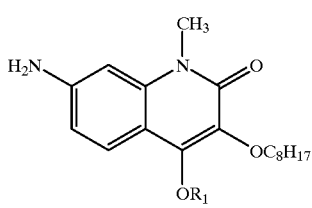

(III)

(wherein $R_1$ is a glycosyl group selected from the group consisting of a glucuronyl group, a glucosyl group, a galactosyl group and a mannosyl group, in which a hydroxyl group is unprotected or protected with an acyl group having a carbon number of 2 to 7 or a benzyl group),
comprising the step of reducing a quinolinone glycoside expressed by general formula (II):

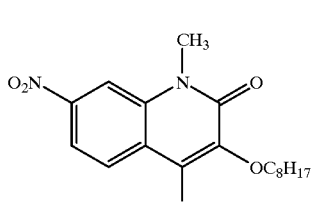

(II)

(wherein, in the formula, $R_1$ is a glycosyl group selected from the group consisting of a glucuronyl group, a glucosyl group, a galactosyl group and a mannosyl group, in which a hydroxyl group is unprotected or protected with an acyl group having a carbon number of 2 to 7 or a benzyl group) in the presence of hydrogen and/or a metallic catalyst;

(20) a process for producing a quinolinone glycoside expressed by general formula (I):

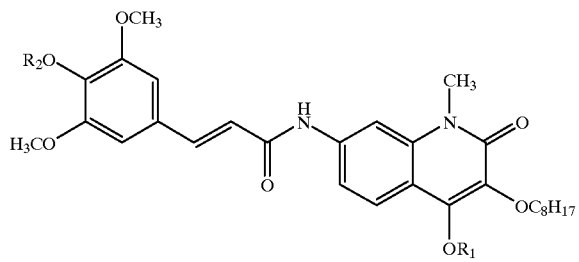

(I)

(wherein each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which a hydroxyl group is unprotected or protected with an acyl group having a carbon number of 2 to 7 or a benzyl group), the process comprising the step of conducting amidation between a quinolinone glycoside expressed by general formula (III):

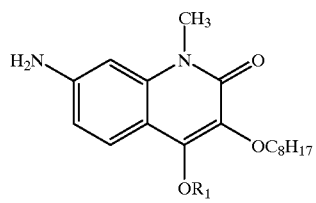

(III)

(wherein $R_1$ is a glycosyl group selected from the group consisting of a glucuronyl group, a glucosyl group, a galactosyl group and a mannosyl group, in which a hydroxyl group is unprotected or protected with an acyl group having a carbon number of 2 to 7 or a benzyl group), and a sinapic acid derivative expressed by general formula (VII):

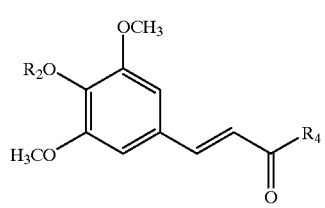

(VII)

(wherein $R_2$ is a hydrogen atom or a glycosyl group selected from the group consisting of a glucuronyl group, a glucosyl group, a galactosyl group and a mannosyl group, in which a hydroxyl group is protected or unprotected, and $R_4$ is a hydroxyl group or a halogen atom);

(21) a process for producing a quinolinone glycoside expressed by general formula (I):

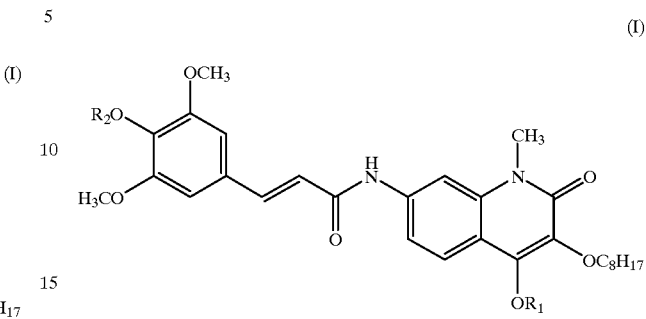

(I)

(wherein each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which a hydroxyl group is unprotected or protected with an acyl group having a carbon number of 2 to 7 or a benzyl group), comprising the steps of:

reacting a quinolinone derivative expressed by general formula (VI):

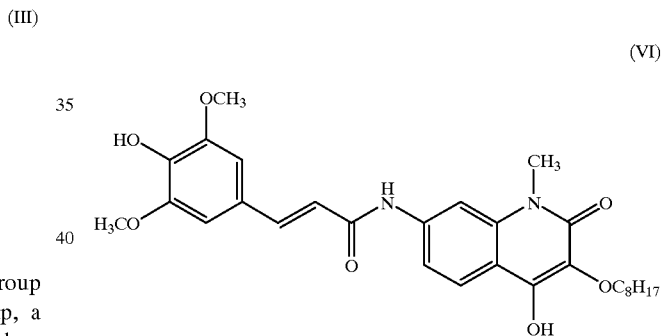

(VI)

with a basic substance; and then conducting a glycosylation reaction with a glycosyl halide, which is obtained by substituting a hydrogen atom at 1-position of a glycose, selected from the group consisting of glucuronic acid, glucose, galactose and mannose, by a halogen atom, and in which a hydroxyl group is protected with an acyl group having a carbon number of 2 to 7 or a benzyl group;

(22) a process for producing a quinolinone glycoside expressed by general formula (I) in which no hydroxyl group in the glycosyl group is protected, comprising the step of eliminating a protecting group in a glycosyl group in a quinolinone glycoside expressed by general formula (I) in which a hydroxyl group in the glycosyl group is protected (I)

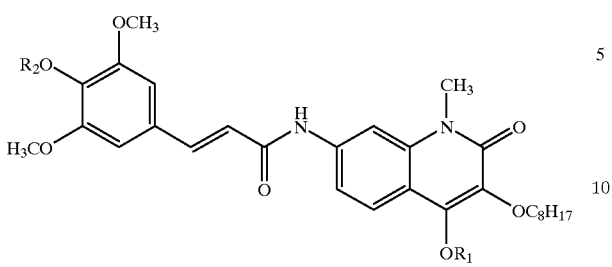

(wherein each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which a hydroxyl group is unprotected or protected with an acyl group having a carbon number of 2 to 7 or a benzyl group).

(23) a process for producing a sinapic acid glycoside expressed by general formula (V):

(V)

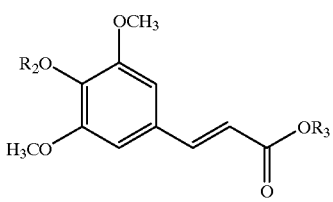

(wherein $R_2$ is a glycosyl group selected from the group consisting of a glucuronyl group, a glucosyl group, a galactosyl group and a mannosyl group, in which a hydroxyl group in the glycosyl group is unprotected or protected with an acyl group having a carbon number of 2 to 7 or a benzyl group, and $R_3$ is selected from the group consisting of a hydrogen atom, an alkyl group, an aryl group and an aralkyl group), comprising the steps of: reacting a sinapic acid ester with a basic substance; and then conducting a glycosylation reaction with a glycosyl halide, which is obtained by substituting a hydrogen atom at 1-position of a hexose, selected from the group consisting of glucuronic acid, glucose, galactose and mannose, by a halogen atom, and in which a hydroxyl group is protected with an acyl group having a carbon number of 2 to 7 or a benzyl group;

(24) a sinapic acid glycoside expressed by general formula (V):

(V)

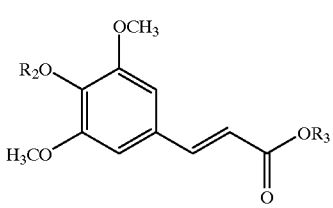

(wherein $R_2$ is a glycosyl group selected from the group consisting of a glucuronyl group, a glucosyl group, a galactosyl group and a mannosyl group, in which a hydroxyl group in the glycosyl group is unprotected or protected with an acyl group having a carbon number of 2 to 7 or a benzyl group, and $R_3$ is selected from the group consisting of a hydrogen atom, an alkyl group, an aryl group and an aralkyl group); and

(25) a method of treating an allergic disease of a mammal, the method comprising administering a pathologically effective amount of a quinolinone glycoside or a physiologically acceptable salt thereof as in any one of (2) and (4) to (10).

DESCRIPTION OF THE PREFERRED EMBODIMENTS

The present invention includes quinolinone glycosides expressed by general formula (I) and their physiologically acceptable salts, wherein, each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which a hydroxyl group in the glycosyl group is protected or unprotected.

A hexose which can be a material for a glycosyl group in any one of the quinolinone glycosides expressed by general formula (I), nitroquinolinone glycosides expressed by general formula (II) and aminoquinolinone glycosides expressed by general formula (III) according to the present invention is glucuronic acid, glucose, galactose or mannose, in which a hydroxyl group in any of these glycosides may or may not be protected with a protecting group. In addition, although there are both D-form and L-form stereoisomers of these hexoses, either stereoisomer may be introduced into the compounds of the present invention.

The quinolinone glycoside represented by general formula (I), (II) or (III) according to the present invention is a compound in which the glycosidic linkage is formed with one of these hexoses at the hydroxyl group at 4-position of a quinolinone derivative and/or at a hydroxyl group in a sinapinoyl group. Although there are two types of glycosidic linkage, namely, α-linkage and β-linkage, the quinolinone glycosides of the present invention include compounds having either type of linkage.

As the protecting group used in the present invention for a hydroxyl group in the glycosyl group, one which is generally used as a protecting group for a saccharide can be used, and, for example, an acyl group, a benzyl group or the like is suitable. Examples of acyl groups are: an alkanoyl group such as an acetyl group, a propionyl group, a butyryl group and an isobutyryl group; an aroyl group such as a benzoyl group and a benzoyl group having a substituent group (for example, p-methoxybenzoyl group, p-methylbenzoyl group, p-chlorobenzoyl group and p-nitrobenzoyl group); and a alkoxycarbonyl group (for example, a methoxycarbonyl group and an ethoxycarbonyl group. An acyl group having a carbon number of 2 to 7 is particularly preferable.

The nitroquinolinone glycosides expressed by general formula (II) according to the present invention are quinolinone glycosides in which, in the formula, $R_1$ is a glycosyl group selected from the group consisting of a glucuronyl group, a glucosyl group, a galactosyl group and a mannosyl group, in which a hydroxyl group in the glycosyl group is protected or unprotected. Physiologically acceptable salts of the nitroquinolinone glycosides are also included in the present invention. Quinolinone glycosides having a glycosyl group derived from either a D-form or an L-form stereoisomer of hexose are included in the quinolinone glycosides of the present invention. In addition, compounds having either an α- or a β- glycosidic linkage are included in the quinolinone glycosides of the present invention. As a protecting group for a hydroxyl group in the glycosyl group, the above-described protecting group for a saccharide can be used, and an acyl group having a carbon number of 2 to 7 is particularly preferable.

The aminoquinolinone glycosides expressed by general formula (III) according to the present invention are quinolinone glycosides in which, in the formula, $R_1$ is a glycosyl group selected from the group consisting of a glucuronyl group, a glucosyl group, a galactosyl group and a mannosyl group, in which a hydroxyl group is protected or unprotected. Physiologically acceptable salts of the aminoquinolinone glycosides are also included in the present invention. These compounds can be obtained by reducing the nitro group in the nitroquinolinone glycoside expressed general formula (II).

Quinolinone glycosides having as $R_1$ a glycosyl group derived from either a D-form or an L-form stereoisomer of hexose are included in the quinolinone glycosides of the present invention. In addition, compounds having either an α- or a β-glycosidic linkage are included in the quinolinone glycosides of the present invention. As a protecting group for a hydroxyl group in the glycosyl group, the above-described protecting group for a saccharide can be used, and an acyl group having a carbon number of 2 to 7 is particularly preferable.

Sinapic acid glycosides expressed by general formula (V) according to the present invention are sinapic acid glycosides in which $R_2$ is a glycosyl group selected from the group consisting of a glucuronyl group, a glucosyl group, a galactosyl group and a mannosyl group, in which a hydroxyl group in the glycosyl group is protected or unprotected, and $R_3$ is a hydrogen atom, an alkyl group, an aryl group or an aralkyl group. Physiologically acceptable salts of the sinapic acid glycosides are also included in the present invention.

Sinapic acid glycosides having as $R_2$ a glycosyl group derived from either a D-form or an L-form stereoisomer of hexose are included in the sinapic acid glycosides of the present invention. In addition, compounds having either an α- or a β- glycosidic linkage are included in the sinapic acid glycosides of the present invention. As a protecting group for a hydroxyl group in the glycosyl group, the above-described protecting group for a saccharide can be used, and an acyl group having a carbon number of 2 to 7 is particularly preferable. $R_3$ is an hydrogen atom, an alkyl group, an aryl group or an aralkyl group.

Examples of the alkyl group are a methyl group, an ethyl group, a propyl group, a butyl group and an alkyl group having a substituent group, such as a trichloroethyl group. As the aryl group, a phenyl group is preferable. Examples of the aralkyl group are a benzyl group and a benzyl group having a substituent group, such as p-hydroxybenzyl group and p-methylbenzyl group; a benzyl group is particularly preferable. Sinapic acid derivatives represented by general formula (VII) according to the present invention are glycosides or their physiologically acceptable salts, in which, in the formula, $R_2$ is a hydrogen atom or a glycosyl group selected from the group consisting of a glucuronyl group, a glucosyl group, a galactosyl group and a mannosyl group, in which a hydroxyl group is protected or unprotected, and $R_4$ is a hydroxyl group or a halogen atom.

Sinapic acid derivatives having as $R_2$ a glycosyl group derived from either a D-form or an L-form stereoisomer of hexose are included in the sinapic acid derivatives of the present invention. In addition, compounds having either an α- or a β- glycosidic linkage are included in the sinapic acid derivatives of the present invention. As a protecting group for a hydroxyl group in the glycosyl group, the above-described protecting group for a saccharide can be used, and an acyl group having a carbon number of 2 to 7 is particularly preferable. $R_4$ is a hydroxyl group or a halogen atom. Examples of the halogen atom are a chlorine atom, a bromine atom and a iodine atom, among which the chlorine atom is particularly preferable.

Next, processes for producing quinolinone glycosides according to the present invention will be explained in detail. The glycoside expressed by general formula (I) can be produced in line with the following reaction path.

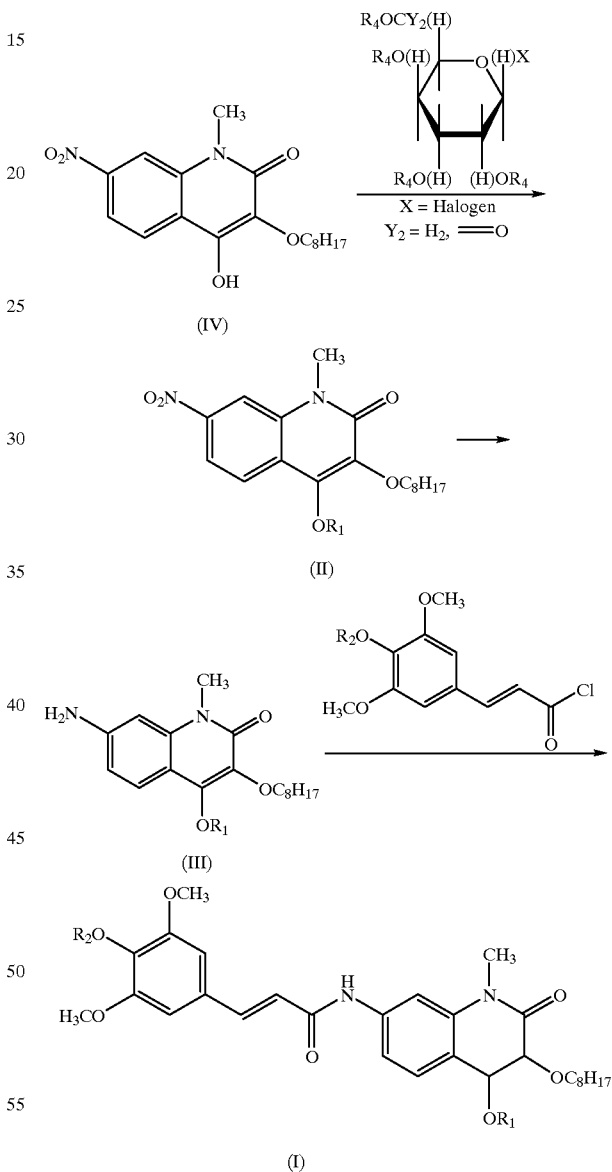

The definitions of $R_1$ and $R_2$ explained for general formulae (I), (II), (III) and (IV) individually are also applied to $R_1$ and $R_2$ in the general formulae (I), (II), (III) and (IV) in the above reaction path. $R_4$ represents an acyl group or an benzyl group as a protecting group for a hydroxyl group in the hexose.

First, glycosylation reaction of the hydroxyl group at 4-position of a quinolinone derivative (IV), which may be prepared by the process disclosed in the Japanese Patent Application, First Publication (Kokai), No. Hei 9-255659 by the present inventors, is conducted. This glycosylation process can be implemented in the presence of a basic substance by reacting the quinolinone derivative (IV) with a halide of a hexose in which hydroxyl groups are protected.

Examples of the basic substance used are: alkaline metal hydrides such as sodium hydride and potassium hydride; alkaline earth metal hydride such as calcium hydride; amines such as DBN (1,5-diazabicyclo[4.3.0]non-5-ene), DBU (1,8-diazabicyclo[5.4.0]undec-7-ene) and DABCO (1,4-diazabicyclo[2.2.2]octane).

Preferable solvents for the reaction are: ether-type solvents such as diethyl ether, tetrahydrofuran and dioxane; and amide-type solvents such as N,N-dimethylformamide, N,N-dimethylacetamide and 1-methyl-2-pyrrolidinone. Although the reaction may proceed at a temperature in the range of −10° C. to 50° C., a temperature in the range of 20° C. to 40° C. is preferable. The reaction is normally completed in 1 to 12 hours so as to yield the nitroquinolinone glycoside of general formula (II), although the period of time varies depending on the basic substance used, the reaction temperature and the solvent.

When a compound in which no hydroxyl group in the glycosyl group is protected is synthesized, a deprotection reaction is additionally conducted by a deacylation reaction or debenzylation reaction for the hexose portion of the compound of general formula (II). The deacylation reaction and the debenzylation reaction may be known conventional ones. That is, in the case of the deacylation, the reaction takes place with a base, as a deacylation agent, such as hydroxides (such as sodium hydroxide, potassium hydroxide and lithium hydroxide) and metal alkoxide (such as sodium methoxide, potassium methoxide sodium ethoxide and potassium ethoxide).

Preferable solvents for this reaction are: lower alcohols such as methanol, ethanol and propanol; ether-type solvents such as diethyl ether, tetrahydrofuran, dimethoxyethane and dioxane; and amide-type solvents such as N,N-dimethylformamide, N,N-dimethylacetamide and 1-methyl-2-pyrrolidinone. The reaction temperature is preferably in the range of −10° C. to 50° C., and more preferably in the range of 0° C. to 30° C., although the temperature varies depending on the reaction reagent and reaction solvent used. The reaction time is normally 1 to 5 hours.

In the case of debenzylation, the reaction is conducted by way of a hydrogenolysis reaction using a metallic catalyst under a hydrogen gas atmosphere. Examples of the metallic catalyst used are palladium, platinum and rhodium. A palladium catalyst is particularly preferable. The amount of catalyst used may be 1 to 10% by weight, with respect to the compound expressed by general formula (II). The reaction may proceed under atmospheric pressure, although the reaction may be conducted under a pressurized hydrogen gas atmosphere.

Preferable solvents for the reaction are: alcohol-type solvents such as methanol, ethanol, propanol and butanol; ether-type solvents such as diethyl ether, tetrahydrofuran and dioxane; and acetate ester-type solvents such as methyl acetate, ethyl acetate and propyl acetate. Although the reaction may proceed at a temperature in the range of −10° C. to 50° C., a temperature in the range of 0° C. to 30° C. is preferable. The reaction is normally completed in 1 to 5 hours. For the purpose of the reaction of the subsequent step, it is normally preferable that hydroxyl groups in the glycosyl group are protected.

Then, by conducting a reaction to reduce a nitro group in the nitroquinolinone glycoside represented by general formula (II), the aminoquinolinone glycoside expressed by general formula (III) is obtained. This reduction reaction may be conducted via hydrogenation reduction under a hydrogen gas atmosphere similar to that described for debenzylation. Alternatively, the reduction reaction may be conducted by a reaction with a metallic catalyst such as tin and zinc. The reduction reaction by reaction with a metallic catalyst can be implemented by allowing a reaction with a metallic catalyst, preferably tin or zinc, to occur in an organic solvent.

Preferable organic solvents used are: alcohol-type solvents such as methanol, ethanol, propanol, isopropanol and butanol; ether-type solvents such as diethyl ether, tetrahydrofuran and dioxane; amide-type solvents such as N,N-dimethylformamide, N,N-dimethylacetamide and 1-methyl-2-pyrrolidinone; organic acids such as formic acid, acetic acid and propionic acid. One of these solvents may be used alone or a mixture of a plurality of solvents may also be used.

In addition, a substance which promotes the reaction, such as hydrochloric acid and calcium chloride, may be added. The reaction temperature is normally in the range of 0° C. to 10° C., and preferably in the range of 30° C. to 80° C., although the temperature varies depending on the metal and reaction solvent used. The reaction time is normally 1 to 5 hours.

Next, glycosidation of the sinapic acid derivative will be explained. This reaction is conducted after protecting a carboxyl group in the sinapic acid portion with an ester group. The ester group may be one conventionally used such as a methyl ester group, an ethyl ester group and a propyl ester group. Alternatively, the ester group may be a substituted alkyl group such as a 2,2,2-trichloroethyl ester group. The glycosidation reaction is conducted in an organic solvent in the presence of a basic substance by reacting the sinapic acid ester with a halide of a hexose.

Examples of the basic substance used are: alkaline metal hydrides such as sodium hydride and potassium hydride; alkaline earth metal hydride such as calcium hydride; amines such as DBN (1,5-diazabicyclo[4.3.0]non-5-ene), DBU (1,8-diazabicyclo[5.4.0]undec-7-ene) and DABCO (1,4-diazabicyclo[2.2.2]octane).

Preferable organic solvents used in which the reaction takes place are: ether-type solvents such as diethyl ether, tetrahydrofuran and dioxane; and amide-type solvents such as N,N-dimethylformamide, N,N-dimethylacetamide and 1-methyl-2-pyrrolidinone. Although the reaction may proceed at a temperature in the range of −10° C. to 50° C., a temperature in the range of 20° C. to 40° C. is preferable. The reaction is normally completed in 1 to 12 hours, although the period of time varies depending on the temperature and the basic substance and solvent used.

Then, a reaction to eliminate the ester group is conducted. In the case where the ester group is a 2,2,2-trichloroethyl ester group, for example, the elimination reaction is performed by a reaction with a zinc powder in acetic acid. Although the reaction may proceed at a temperature in the range of 0° C. to 80° C., a preferable reaction temperature is in the range of 20° C. to 50° C. The reaction is normally completed in 1 to 5 hours. Then, carboxyl groups in the sinapic acid glycoside obtained are reacted with thionyl chloride, for example, or the like, to yield an acid halide.

Then, an amidation reaction between the thus-obtained acid halide of sinapic acid glycoside and the aminoquinolinone glycoside expressed by general formula (III) is conducted. An organic solvent is used for the reaction. Preferable solvents used are, for example, halogen-type solvents such as methylene chloride and chloroform; ether-type solvents such as diethyl ether, tetrahydrofuran, dimethoxyethane and dioxane; and acetate ester-type solvents such as methyl acetate, ethyl acetate and propyl acetate.

In this amidation reaction, a basic substance may be added as a substance which promotes the reaction. Preferable basic substances are amines such as triethylamine, pyridine and collidine. Although the reaction may proceed at a temperature in the range of −10° C. to 50° C., a preferable temperature is in the range of 0° C. to 30° C. The reaction is normally completed in 1 to 5 hours. The amidation reaction can be conducted by a dehydration condensation between a simply deesterified sinapic acid glycoside, not necessarily obtained via an acid halide of the sinapic acid glycoside, and the aminoquinolinone glycoside represented by general formula (III).

Finally, by eliminating the protecting group for the glycosyl group in the quinolinone glycoside expressed by general formula (I), if necessary, the desired quinolinone glycoside is obtained. This elimination reaction can be conducted in accordance with the above-described method, that is, by a debenzylation or deacylation reaction.

As another process for producing the quinolinone glycoside expressed by general formula (I) of the present invention, the quinolinone derivative which is disclosed in the Japanese Patent Application, First Publication (Kokai), No. Hei 9-255659 and which is expressed by general formula (VI), that is, 7-(3,5-dimethoxy-4-hydroxycinnamoyl)amino-4-hydroxy-1-methyl-3-octyloxy-2(1H)-quinolinone, may be glycosylated by a direct reaction with a glycosyl halide which has a halogen group at 1-position and in which hydroxyl groups are protected.

(VI)

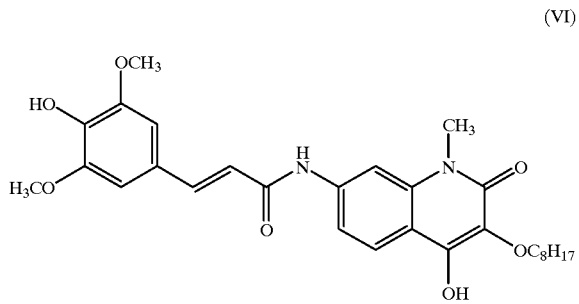

The type of the glycosyl halide selected from the group consisting of glucuronic acid, glucose, galactose and mannose, which has a halogen group at 1-position and in which hydroxyl groups are protected, the reaction solvent, the reaction reagent, the reaction conditions and the like to be employed for this glycosylation reaction are similar to those described above. In addition, in order to obtain a quinolinone glycoside in which no hydroxyl group in the glycosyl group is protected, the protecting group may be eliminated in a manner similar to that described above.

The following compounds are illustrative examples of the thus obtained glycosyloxyquinolinone derivatives represented by the formula (I) of the present invention. 7-[3,5-dimethoxy-4-(6-O-methyl-2,3,4-triacetyl-β-D-glucuropyranosyloxy)cinnamoyl]amino-3-octyloxy-4-(6-O-methyl-2,3,4-triacetyl-β-D-glucuropyranosyloxy)-1-methyl-2(1H)-quinolinone, 7-[3,5-dimethoxy-4-(6-O-methyl-2,3,4-triacetyl-β-D-glucuropyranosyloxy)cinnamoyl]amino-3-octyloxy-4-hydroxy-1-methyl-2(1H)-quinolinone, 7-[(3,5-dimethoxy-4-hydroxycinnamoyl)amino]-3-octyloxy-4-(6-O-methyl-2,3,4-triacetyl-β-D-glucuropyranosyloxy)-1-methyl-2(1H)-quinolinone, 7-[3,5-dimethoxy-4-(tetra-O-acetyl-β-D-glucopyranosyloxy)cinnamoyl]amino-3-octyloxy-4-(tetra-O-acetyl-β-D-glucopyranosyloxy)-1-methyl-2(1H)-quinolinone, 7-[3,5-dimethoxy-4-(tetra-O-acetyl-β-D-glucopyranosyloxy)cinnamoyl]amino-3-octyloxy-4-hydroxy-1-methyl-2(1H)-quinolinone, 7-(3,5-dimethoxy-4-hydroxycinnamoyl)amino-3-octyloxy-4-(tetra-O-acetyl-β-D-glucopyranosyloxy)-1-methyl-2(1H)-quinolinone, 7-[3,5-dimethoxy-4-(tetra-O-acetyl-β-D-galactopyranosyloxy)cinnamoyl]amino-3-octyloxy-4-(tetra-O-acetyl-β-D-galactopyranosyloxy)-1-methyl-2(1H)-quinolinone, 7-[3,5-dimethoxy-4-(tetra-O-acetyl-β-D-galactopyranosyloxy)cinnamoyl]amino-3-octyloxy-4-hydroxyl-methyl-2(1H)-quinolinone, 7-[3,5-dimethoxy-4-hydroxycinnamoyl)amino]-3-octyloxy-4-(tetra-O-acetyl-β-D-galactopyranosyloxy)-1-methyl-2(1H)-quinolinone, 7-[3,5-dimethoxy-4-(tetra-O-acetyl-β-D-mannopyranosyloxy)cinnamoyl]amino-3-octyloxy-4-(tetra-O-acetyl-α-D-mannopyranosyloxy)-1-methyl-2(1H)-quinolinone, 7-[3,5-dimethoxy-4-(tetra-O-acetyl-α-D-mannopyranosyloxy)cinnamoyl]amino-3-octyloxy-4-hydroxyl-methyl-2(1H)-quinolinone, 7-(3,5-dimethoxy-4-hydroxycinnamoyl)amino-3-octyloxy-4-(tetra-O-acetyl-α-D-mannopyranosyloxy)-1-methyl-2(1H)-quinolinone, 7-[3,5-dimethoxy-4-(6-O-methyl-2,3,4-teibenzoyl-β-D-glucuropyranosyloxy)cinnamoyl]amino-3-octyloxy-4-(6-O-methyl-2,3,4-teibenzoyl-β-D-glucuropyranosyloxy)-1-methyl-2(1H)-quinolinone, 7-[3,5-dimethoxy-4-(6-O-methyl-2,3,4-teibenzoyl-β-D-glucuropyranosyloxy)cinnamoyl]amino-3-octyloxy-4-hydroxyl-methyl-2(1H)-quinolinone, 7-(3,5-dimethoxy-4-hydroxycinnamoyl)amino-3-octyloxy-4-(6-O-methyl-2,3,4-teibenzoyl-β-D-glucuropyranosyloxy)-1-methyl-2(1H)-quinolinone, 7-[3,5-dimethoxy-4-(tetra-O-benzoyl-β-D-glucopyranosyloxy)cinnamoyl]amino-3-octyloxy-4-(tetra-O-benzoyl-β-D-glucopyranosyloxy)-1-methyl-2(1H)-quinolinone, 7-[3,5-dimethoxy-4-(tetra-O-benzoyl-β-D-glucopyranosyloxy)cinnamoyl]amino-3-octyloxy-4-hydroxyl-methyl-2(1H)-quinolinone, 7-[(3,5-dimethoxy-4-hydroxycinnamoyl)amino]-3-octyloxy-4-(tetra-O-benzoyl-β-D-glucopyranosyloxy)-1-methyl-2(1H)-quinolinone, 7-[3,5-dimethoxy-4-(tetra-O-benzoyl-β-D-galactopyranosyloxy)cinnamoyl]amino-3-octyloxy-4-(tetra-O-benzoyl-β-D-galactopyranosyloxy)-1-methyl-2(1H)-quinolinone, 7-[3,5-dimethoxy-4-(tetra-O-benzoyl-β-D-galactopyranosyloxy)cinnamoyl]amino-3-octyloxy-4-hydroxyl-methyl-2(1H)-quinolinone, 7-(3,5-dimethoxy-4-hydroxycinnamoyl)amino-3-octyloxy-4-(tetra-O-benzoyl-β-D-galactopyranosyloxy)-1-methyl-2(1H)-quinolinone, 7-[3,5-dimethoxy-4-(tetra-O-benzoyl-α-D-mannopyranosyloxy)cinnamoyl]amino-3-octyloxy-4-(tetra-O-benzoyl-α-D-mannopyranosyloxy)-1-methyl-2(1H)-quinolinone, 7-[3,5-dimethoxy-4-(tetra-O-benzoyl-α-D-mannopyranosyloxy)cinnamoyl]amino-3-octyloxy-4-hydroxyl-methyl-2(1H)-quinolinone, 7-[3,5-dimethoxy-4-hydroxycinnamoyl)amino-3-octyloxy-4-(tetra-O-benzoyl-α-D-mannopyranosyloxy)-1-methyl-2(1H)-quinolinone, 7-[3,5-dimethoxy-4-(6-O-methyl-2,3,4-tribenzyl-β-D-glucuropyranosyloxy)cinnamoyl]amino-3-octyloxy-4-(6-O-methyl-2,3,4-tribenzyl-β-D-glucuropyranosyloxy)-1-methyl-2(1H)-quinolinone, 7-[3,5-dimethoxy-4-(6-O-methyl-2,3,4-tribenzyl-β-D-glucuropyranosyloxy)

cinnamoyl]amino-3-octyloxy-4-hydroxyl-methyl-2(1H)-quinolinone, 7-(3,5-dimethoxy-4-hydroxycinnamoyl) amino-3-octyloxy-4-(6-O-methyl-2,3,4-tribenzyl-β-D-glucuropyranosyloxy)-1-methyl-2(1H)-quinolinone, 7-[3,5-dimethoxy-4-(tetra-O-benzyl-β-D-glucopyranosyloxy) cinnamoyl]amino-3-octyloxy-4-(tetra-O-benzyl-β-D-glucopyranosyloxy)-1-methyl-2(1H)-quinolinone, 7-[3,5-dimethoxy-4-(tetra-O-benzyl-β-D-glucopyranosyloxy) cinnamoyl]amino-3-octyloxy-4-hydroxyl-methyl-2(1H)-quinolinone, 7-(3,5-dimethoxy-4-hydroxycinnamoyl) amino-3-octyloxy-4-(tetra-O-benzyl-β-D-glucopyranosyloxy)-1-methyl-2(1H)-quinolinone, 7-[3,5-dimethoxy-4-(tetra-O-benzyl-β-D-galactopyranosyloxy) cinnamoyl]amino-3-octyloxy-4-(tetra-O-benzyl-β-D-galactopyranosyloxy)-1-methyl-2(1H)-quinolinone, 7-[3,5-dimethoxy-4-(tetra-O-benzyl-β-D-galactopyranosyloxy) cinnamoyl]amino-3-octyloxy-4-hydroxyl-methyl-2(1H)-quinolinone, 7-[3,5-dimethoxy-4-hydroxycinnamoyl) amino]-3-octyloxy-4-(tetra-O-benzyl-β-D-galactopyranosyloxy)-1-methyl-2(1H)-quinolinone, 7-[3,5-dimethoxy-4-(tetra-O-benzyl-α-D-mannopyranosyloxy) cinnamoyl]amino-3-octyloxy-4-(tetra-O-benzyl-α-D-mannopyranosyloxy)-1-methyl-2(1H)-quinoline, 7-[3,5-dimethoxy-4-(tetra-O-benzyl-α-D-mannopyranosyloxy) cinnamoyl]amino-3-octyloxy-4-hydroxyl-methyl-2(1H)-quinolinone, 7-(3,5-dimethoxy-4-hydroxycinnamoyl) amino-3-octyloxy-4-(tetra-O-benzyl-α-D-mannopyranosyloxy)-1-methyl-2(1H)-quinolinone, 7-[3,5-dimethoxy-4-(β-D-glucuropyranosyloxy)cinnamoyl]amino-3-octyloxy-4-(β-D-glucuropyranosyloxy)-1-methyl-2(1H)-quinolinone, 7-[3,5-dimethoxy-4-(β-D-glucuropyranosyloxy)cinnamoyl]amino-3-octyloxy-4-hydroxyl-methyl-2(1H)-quinolinone, 7-(3,5-dimethoxy-4-hydroxycinnamoyl)amino-3-octyloxy-4-(β-D-glucuropyranosyloxy)-1-methyl-2(1H)-quinolinone, 7-[3,5-dimethoxy-4-(β-D-glucopyranosyloxy)cinnamoyl]amino-3-octyloxy-4-(β-D-glucopyranosyloxy)-1-methyl-2(1H)-quinolinone, 7-[3,5-dimethoxy-4-(β-D-glucopyranosyloxy)cinnamoyl]amino-3-octyloxy-4-hydroxyl-methyl-2(1H)-quinolinone, 7-(3,5-dimethoxy-4-hydroxycinnamoyl) amino-3-octyloxy-4-(β-D-glucopyranosyloxy)-1-methyl-2(1H)-quinolinone, 7-[3,5-dimethoxy-4-(β-D-galactopyranosyloxy)cinnamoyl]amino-3-octyloxy-4-(β-D-galactopyranosyloxy)-1-methyl-2(1H)-quinolinone, 7-[3,5-dimethoxy-4-(β-D-galactopyranosyloxy)cinnamoyl]amino-3-octyloxy-4-hydroxyl-methyl-2(1H)-quinolinone, 7-(3,5-dimethoxy-4-hydroxycinnamoyl)amino-3-octyloxy-4-(β-D-galactopyranosyloxy)-1-methyl-2(1H)-quinolinone, 7-[3,5-dimethoxy-4-(α-D-mannopyranosyloxy)cinnamoyl]amino-3-octyloxy-4-(α-D-mannopyranosyloxy)-1-methyl-2(1H)-quinolinone, 7-[3,5-dimethoxy-4-(α-D-mannopyranosyloxy)cinnamoyl]amino-3-octyloxy-4-hydroxyl-methyl-2(1H)-quinolinone, 7-(3,5-dimethoxy-4-hydroxycinnamoyl)amino-3-octyloxy-4-(α-D-mannopyranosyloxy)-1-methyl-2(1H)-quinolinone, and physiologically acceptable salts of these compounds are also included in the illustrative example.

The term "physiologically acceptable salts" as used herein means nontoxic alkali addition salts of, for example, the compounds cited above, which include sodium salts, potassium salts, magnesium salts, calcium salts ammonium salts, nontoxic amine salts and the like.

These physiologically acceptable salts can be produced by known methods and are also included in the present invention.

The following compounds are illustrative examples of the thus obtained glycosyloxyquinolinone derivatives represented by the formula (II) of the present invention. 7-nitro-3-octyloxy-4-(6-O-methyl-2,3,4-triacetyl-β-D-glcuropyranosyloxy)-1-methyl-2(1H)-quinolinone, 7-nitro-3-octyloxy-4-(tetra-O-acetyl-β-D-glucopyranosyloxy)-1-methyl-2(1H)-quinolinone, 7-nitro-3-octyloxy-4-(tetra-O-acetyl-β-D-galactopyranosyloxy)-1-methyl-2(1H)-quinolinone, 7-nitro-3-octyloxy-4-(tetra-O-acetyl-α-D-mannopyranosyloxy)-1-methyl-2(1H)-quinolinone, 7-nitro-3-octyloxy-4-(6-O-methyl-2,3,4-tribenzoyl-β-D-glucuropyranosyloxy)-1-methyl-2(1H)-quinolinone, 7-nitro-3-octyloxy-4-(tetra-O-benzoyl--β-D-glucopyranosyloxy)-1-methyl-2(1H)-quinolinone, 7-nitro-3-octyloxy-4-(tetra-O-benzoyl-β-D-galactopyranosyloxy)-1-methyl-2(1H)-quinolinone, 7-nitro-3-octyloxy-4-(tetra-O-benzoy-α-D-mannopyranosyloxy)-1-methyl-2(1H)-quinolinone, 7-nitro-3-octyloxy-4-(6-O-methyl-2,3,4-tribenzyl-β-D-glucuropyranosyloxy)-1-methyl-2(1H)-quinolinone, 7-nitro-3-octyloxy-4-(tetra-O-benzyl-β-D-glucopyranosyloxy)-1-methyl-2(1H)-quinolinone, 7-nitro-3-octyloxy-4-(tetra-O-benzyl-β-D-galactopyranosyloxy)-1-methyl-2(1H)-quinolinone, 7-nitro-3-octyloxy-4-(tetra-O-benzyl-α-D-mannopyranosyloxy)-1-methyl-2(1H)-quinolinone, 7-nitro-3-octyloxy-4-(6-O-methyl-2,3,4-tribenzyl-β-D-glucuropyranosyloxy)-1-methyl-2(1H)-quinolinone, 7-nitro-3-octyloxy-4-(β-D-glucopyranosyloxy)-1-methyl-2(1H)-quinolinone, 7-nitro-3-octyloxy-4-(tetra-O-acetyl-β-D-galactopyranosyloxy)-1-methyl-2(1H)-quinolinone, 7-nitro-3-octyloxy-4-(α-D-mannopyranosyloxy)-1-methyl-2(1H)-quinolinone, and physiologically acceptable salts of these compounds are also included in the illustrative example.

These are synthetic intermediate of useful glycosyloxyquinolinone derivatives represented by the formula (II) as medicine.

The following compounds are illustrative examples of the thus obtained glycosyloxyquinolinone derivatives represented by the formula (III) of the present invention. 7-amino-3-octyloxy-4-(6-O-methyl-2,3,4-triacetyl-β-D-glcuropyranosyloxy)-1-methyl-2(1H)-quinolinone, 7-amino-3-octyloxy-4-(tetra-O-acetyl-β-D-glucopyranosyloxy)-1-methyl-2(1H)-quinolinone, 7-amino-3-octyloxy-4-(tetra-O-acetyl-β-D-galactopyranosyloxy)-1-methyl-2(1H)-quinolinone, 7-amino-3-octyloxy-4-(tetra-O-acetyl-α-D-mannopyranosyloxy)-1-methyl-2(1H)-quinolinone, 7-amino-3-octyloxy-4-(6-O-methyl-2,3,4-tribenzoyl-β-D-glucuropyranosyloxy)-1-methyl-2(1H)-quinolinone, 7-amino-3-octyloxy-4-(tetra-O-benzoyl-β-D-glucopyranosyloxy)-1-methyl-2(1H)-quinolinone, 7-amino-3-octyloxy-4-(tetra-O-benzoyl-β-D-galactopyranosyloxy)-1-methyl-2(1H)-quinolinone, 7-amino-3-octyloxy-4-(tetra-O-benzoyl-α-D-mannopyranosyloxy)-1-methyl-2(1H)-quinolinone, 7-amino-3-octyloxy-4-(6-O-methyl-2,3,4-tribenzyl-β-D-glucuropyranosyloxy)-1-methyl-2(1H)-quinolinone, 7-amino-3-octyloxy-4-(tetra-O-benzyl-β-D-glucopyranosyloxy)-1-methyl-2(1H)-quinolinone, 7-amino-3-octyloxy-4-(tetra-O-benzyl-β-D-galactopyranosyloxy)-1-methyl-2(1H)-quinolinone, 7-amino-3-octyloxy-4-(tetra-O-benzoyl-α-D-mannopyranosyloxy)-1-methyl-2(1H)-quinolinone, 7-amino-3-octyloxy-4-(β-D-glucuropyranosyloxy)-1-methyl-2(1H)-quinolinone, 7-amino-3-octyloxy-4-(β-D-glucopyranosyloxy)-1-methyl-2(1H)-quinolinone, 7-amino-3-octyloxy-4-(β-D-galactopyranosyloxy)-1-methyl-2(1H)-quinolinone, 7-amino-3-octyloxy-4-(a-D-mannopyranosyloxy)-1-methyl-2(1H)-quinolinone, and physiologically acceptable salts of these compounds are also included in the illustrative example.

These are synthetic intermediate of useful glycosyloxyquinolinone derivatives represented by the formula (V) as medicine.

3,5-dimethoxy-4-(6-O-methyl-2,3,4-triacetyl-β-D-glucuropyranosyloxy)cinnamic acid, Methyl[3,5-dimethoxy-4-(6-O-methyl-2,3,4-triacetyl-β-D-glucuropyranosyloxy)]cinnamate, Ethyl[3,5-dimethoxy-4-(6-O-methyl-2,3,4-triacetyl-β-D-glucuropyranosyloxy)cinnamate, 1,1,1-Trichloroethyl[3,5-dimethoxy-4-(6-O-methyl-2,3,4-triacetyl-β-D-glucuropyranosyloxy)cinnamate, Phenyl[3,5-dimethoxy-4-(6-O-methyl-2,3,4-triacetyl-β-D-glucuropyranosyloxy)]cinnamate, Benzyl[3,5-dimethoxy-4-(6-O-methyl-2,3,4-triacetyl-β-D-glucuropyranosyloxy)]cinnamate, 3,5-dimethoxy-4-(tetra-O-acetyl-β-D-glucopyranosyloxy) cinnamic acid, Methyl[3,5-dimethoxy-4-(tetra-O-acetyl-β-D-glucopyranosyloxy)]cinnamate, Ethyl[3,5-dimethoxy-4-(tetra-O-acetyl-β-D-glucopyranosyloxy)]cinnamate, 1,1,1-Trichloroethyl[3,5-dimethoxy-4-(tetra-O-acetyl-β-D-glucopyranosyloxy)]cinnamate, Phenyl[3,5-dimethoxy-4-(tetra-O-acetyl-β-D-glucopyranosyloxy)]cinnamate, Benzyl[3,5-dimethoxy-4-(tetra-O-acetyl-β-D-glucopyranosyloxy)]cinnamate, 3,5-dimethoxy-4-(tetra-O-acetyl-β-D-galactopyranosyloxy)cinnamic acid, Methyl [3,5-dimethoxy-4-(tetra-O-acetyl-β-D-galactopyranosyloxy)]cinnamate, Ethyl[3,5-dimethoxy-4-(tetra-O-acetyl-β-D-galactopyranosyloxy)]cinnamate, 1,1,1-Trichloroethyl[3,5-dimethoxy-4-(tetra-O-acetyl-β-D-galactopyranosyloxy)]cinnamate, Phenyl[3,5-dimethoxy-4-(tetra-O-acetyl-β-D-galactopyranosyloxy)]cinnamate, Benzyl[3, 5-dimethoxy-4-(tetra-O-acetyl-β-D-galactopyranosyloxy)]cinnamate, 3,5-dimethoxy-4-(tetra-O-acetyl-α-D-mannopyranosyloxy) cinnamic acid, Methyl [3,5-dimethoxy-4-(tetra-O-acetyl-α-D-mannopyranosyloxy)]cinnamate, Ethyl[3,5-dimethoxy-4-(tetra-O-acetyl-α-D-mannopyranosyloxy)]cinnamate, 1,1,1-Trichloroethyl[3,5-dimethoxy-4-(tetra-O-acetyl-α-D-mannopyranosyloxy)]cinnamate, Phenyl[3,5-dimethoxy-4-(tetra-O-acetyl-α-D-mannopyranosyloxy)]cinnamate, Benzyl[3,5-dimethoxy-4-(tetra-O-acetyl-α-D-mannopyranosyloxy)]cinnamate, 3,5-dimethoxy-4-(6-O-methyl-2,3,4-tribenzoyl-β-D-glucuropyranosyloxy) cinnamic acid, Methyl[3,5-dimethoxy-4-(6-O-methyl-2,3,4-tribenzoyl-β-D-glucuropyranosyloxy)]cinnamate, Ethyl[3,5-dimethoxy-4-(6-O-methyl-2,3,4-tribenzoyl-β-D-glucuropyranosyloxy)]cinnamate, 1,1,1-Trichloroethyl[3,5-dimethoxy-4-(6-O-methyl-2,3,4-tribenzoyl-β-D-glucuropyranosyloxy)]cinnamate, 3,5-dimethoxy-4-(tetra-O-benzoyl-β-D-glucopyranosyloxy)cinnamic acid, Methyl [3,5-dimethoxy-4-(tetra-O-benzoyl-β-D-glucopyranosyloxy)]cinnamate, Ethyl[3,5-dimethoxy-4-(tetra-O-benzoyl-β-D-glucopyranosyloxy)]cinnamate, 1,1,1-Trichloroethyl[3,5-dimethoxy-4-(tetra-O-benzoyl-β-D-glucopyranosyloxy)]cinnamate, Phenyl[3,5-dimethoxy-4-(tetra-O-benzoyl-β-D-glucopyranosyloxy)cinnamate, Benzyl[3,5-dimethoxy-4-(tetra-O-benzoyl-β-D-glucopyranosyloxy)cinnamate, 3,5-dimethoxy-4-(tetra-O-benzoyl-β-D-galactopyranosyloxy)cinnamic acid, Methyl [3,5-dimethoxy-4-(tetra-O-benzoyl-β-D-galactopyranosyloxy)]cinnamate, Ethyl[3,5-dimethoxy-4-(tetra-O-benzoyl-β-D-galactopyranosyloxy)]cinnamate,1,1,1-Trichloroethyl[3,5-dimethoxy-4-(tetra-O-benzoyl-β-D-galactopyranosyloxy)]cinnamate, Phenyl[3,5-dimethoxy-4-(tetra-O-benzoyl-β-D-galactopyranosyloxy)]cinnamate, Benzyl[3,5-dimethoxy-4-(tetra-O-benzoyl-β-D-galactopyranosyloxy)]cinnamate, 3,5-dimethoxy-4-(tetra-O-benzoyl-α-D-mannopyranosyloxy)cinnamic acid, Methyl[3,5-dimethoxy-4-(tetra-O-benzoyl-α-D-mannopyranosyloxy)]cinnamate, Ethyl[3,5-dimethoxy-4-(tetra-O-benzoyl-α-D-mannopyranosyloxy)]cinnamate, 1,1,1-Trichloroethyl[3,5-dimethoxy-4-(tetra-O-benzoyl-α-D-mannopyranosyloxy)]cinnamate, Phenyl[3,5-dimethoxy-4-(tetra-O-benzoyl-α-D-mannopyranosyloxy)]cinnamate, Benzyl[3,5-dimethoxy-4-(tetra-O-benzoyl-α-D-mannopyranosyloxy)]cinnamate, 3,5-dimethoxy-4-(6-O-methyl-2,3,4-tribenzyl-β-D-glucuropyranosyloxy)cinnamic acid, Methyl[3,5-dimethoxy-4-(6-O-methyl-2,3,4-tribenzyl-β-D-glucuropyranosyloxy)]cinnamate, Ethyl[3,5-dimethoxy-4-(6-O-methyl-2,3,4-tribenzyl-β-D-glucuropyranosyloxy)]cinnamate, 1,1,1-Trichloroethyl[3,5-dimethoxy-4-(6-O-methyl-2,3,4-tribenzyl-β-D-glucuropyranosyloxy)]cinnamate, Phenyl[3,5-dimethoxy-4-(6-O-methyl-2,3,4-tribenzyl-β-D-glucuropyranosyloxy)]cinnamate, Benzyl[3,5-dimethoxy-4-(6-O-methyl-2,3,4-tribenzyl-β-D-glucuropyranosyloxy)]cinnamate, 3,5-dimethoxy-4-(tetra-O-benzyl-β-D-glucopyranosyloxy) cinnamic acid, Methyl[3,5-dimethoxy-4-(tetra-O-benzyl-β-D-glucopyranosyloxy)]cinnamate, Ethyl[3,5-dimethoxy-4-(tetra-O-benzyl-β-D-glucopyranosyloxy)]cinnamate, 1,1,1-Trichloroethyl[3,5-dimethoxy-4-(tetra-O-benzyl-β-D-glucopyranosyloxy)]cinnamate, Phenyl[3,5-dimethoxy-4-(tetra-O-benzyl-β-D-glucopyranosyloxy)]cinnamate, Benzyl[3,5-dimethoxy-4-(tetra-O-benzyl-β-D-glucopyranosyloxy)]cinnamate, 3,5-dimethoxy-4-(tetra-O-benzyl-β-D-galactopyranosyloxy)cinnamic acid, Methyl[3,5-dimethoxy-4-(tetra-O-benzyl-β-D-galactopyranosyloxy)]cinnamate, Ethyl[3,5-dimethoxy-4-(tetra-O-benzyl-β-D-galactopyranosyloxy)]cinnamate, 1,1,1-Trichloroethyl[3,5-dimethoxy-4-(tetra-O-benzyl-β-D-galactopyranosyloxy)]cinnamate, Phenyl[3,5-dimethoxy-4-(tetra-O-benzyl-β-D-galactopyranosyloxy)]cinnamate, Benzyl[3,5-dimethoxy-4-(tetra-O-benzyl-β-D-galactopyranosyloxy)]cinnamate, 3,5-dimethoxy-4-(tetra-O-benzyl-α-D-mannopyranosyloxy) cinnamic acid, Methyl[3,5-dimethoxy-4-(tetra-O-benzyl-α-D-mannopyranosyloxy)]cinnamate,Ethyl[3,5-dimethoxy-4-(tetra-O-benzyl-α-D-mannopyranosyloxy)]cinnamate, 1,1,1-Trichloroethyl[3,5-dimethoxy-4-(tetra-O-benzyl-α-D-mannopyranosyloxy)]cinnamate, Phenyl[3,5-dimethoxy-4-(tetra-O-benzyl-α-D-mannopyranosyloxy)]cinnamate, Benzyl[3,5-dimethoxy-4-(tetra-O-benzyl-α-D-mannopyranosyloxy)]cinnamate, 3,5-dimethoxy-4-(β-D-glucuropyranosyloxy)cinnamic acid, Methyl[3,5-dimethoxy-4-(β-D-glucuropyranosyloxy)]cinnamate, Ethyl [3,5-dimethoxy-4-(β-D-glucuropyranosyloxy)]cinnamate, 1,1,1-Trichloroethyl[3,5-dimethoxy-4-(β-D-glucuropyranosyloxy)]cinnamate, Phenyl[3,5-dimethoxy-4-(β-D-glucuropyranosyloxy)]cinnamate, Benzyl[3,5-dimethoxy-4-(β-D-glucuropyranosyloxy)]cinnamate, 3,5-dimethoxy-4-(β-D-glucopyranosyloxy)cinnamic acid, Methyl[3,5-dimethoxy-4-(β-D-glucopyranosyloxy)] cinnamate, Ethyl[3,5-dimethoxy-4-(β-D-glucopyranosyloxy)]cinnamate, 1,1,1-Trichloroethyl[3,5-dimethoxy-4-(β-D-glucopyranosyloxy)]cinnamate, Phenyl [3,5-dimethoxy-4-(β-D-glucopyranosyloxy)]cinnamate, Benzyl[3,5-dimethoxy-4-β-D-glucopyranosyloxy)] cinnamate, 3,5-dimethoxy-4-(β-D-galactopyranosyloxy) cinnamic acid, Methyl[3,5-dimethoxy-4-(β-D-galactopyranosyloxy)]cinnamate, Ethyl[3,5-dimethoxy-4-(β-D-galactopyranosyloxy)]cinnamate, 1,1,1-Trichloroethyl [3,5-dimethoxy-4-(β-D-galactopyranosyloxy)]cinnamate, Phenyl[3,5-dimethoxy-4-(β-D-galactopyranosyloxy)]cinnamate, Benzyl[3,5-dimethoxy-4-(β-D-galactopyranosyloxy)]cinnamate, 3,5-dimethoxy-4-(α-D-mannopyranosyloxy)cinnamic acid, Methyl[3,5-dimethoxy-4-(α-D-mannopyranosyloxy)]cinnamate, Ethyl[3,5- dimethoxy-4-(α-D-mannopyranosyloxy)cinnamate, 1,1,1-Trichloroethhyl[3, 5-dimethoxy-4-(α-D-mannopyranosyloxy)]cinnamate, Phenyl[3,5-dimethoxy-4-(α-D-mannopyranosyloxy)]cinnamate, Benzyl[3,5-dimethoxy-4-(α-D-mannopyranosyloxy)cinnamate, and physiologically acceptable salts of these compounds are also included in the illustrative example.

The following compounds are illustrative examples of the thus obtained glycosyloxycinnamic acid derivatives represented by the formula (VII) of the present invention. 3,5-dimethoxy-4-(6-O-methyl-2,3,4-triacetyl-β-D-glcuropyranosyloxy)cinnamoyl chloride, 3,5-dimethoxy-4-(6-O-methyl-2,3,4-triacetyl-β-D-glcuropyranosyloxy) cinnamoyl bromide, 3,5-dimethoxy-4-(6-O-methyl-2,3,4-triacetyl-β-D-glcuropyranosyloxy)cinnamoyl iodide, 3,5-dimethoxy-4-(tetra-O-acetyl-β-D-glucopyranosyloxy) cinnamoyl chloride, 3,5-dimethoxy-4-(tetra-O-acetyl-β-D-glucopyranosyloxy)cinnamoyl bromide, 3,5-dimethoxy-4-(tetra-O-acetyl-β-D-glucopyranosyloxy)cinnamoyl iodide, 3,5-dimethoxy-4-(tetra-O-acetyl-β-D-galactopyranosyloxy) cinnamoyl chloride, 3,5-dimethoxy-4-(tetra-O-acetyl-β-D-galactopyranosyloxy)cinnamoyl bromide, 3,5-dimethoxy-4-(tetra-O-acetyl-β-D-galactopyranosyloxy)cinnamoyl iodide, 3,5-dimethoxy-4-(tetra-O-acetyl-α-D-mannopyranosyloxy) cinnamoyl chloride, 3,5-dimethoxy-4-(tetra-O-acetyl-α-D-mannopyranosyloxy)cinnamoyl bromide, 3,5-dimethoxy-4-(tetra-O-acetyl-α-D-mannopyranosyloxy)cinnamoyl iodide, 3,5-dimethoxy-4-(6-O-methyl-2,3,4-tribenzoyl-β-D-glucuropyranosyloxy)cinnamoyl chloride, 3,5-dimethoxy-4-(6-O-methyl-2,3,4-tribenzoyl-β-D-glucuropyranosyloxy) cinnamoyl bromide, 3,5-dimethoxy-4-(6-O-methyl-2,3,4-tribenzoyl-β-D-glucuropyranosyloxy)cinnamoyl iodide, 3,5-dimethoxy-4-(tetra-O-benzoyl-β-D-glucopyranosyloxy) cinnamoyl chloride, 3,5-dimethoxy-4-(tetra-O-benzoyl-β-D-glucopyranosyloxy)cinnamoyl bromide, 3,5-dimethoxy-4-(tetra-O-benzoyl-β-D-glucopyranosyloxy)cinnamoyl iodide, 3,5-dimethoxy-4-(tetra-O-benzoyl-β-D-galactopyranosyloxy)cinnamoyl chloride, 3,5-dimethoxy-4-(tetra-O-benzoyl-β-D-galactopyranosyloxy)cinnamoyl bromide, 3,5-dimethoxy-4-(tetra-O-benzoyl-β-D-galactopyranosyloxy)cinnamoyl iodide, 3,5-dimethoxy-4-(tetra-O-benzoyl-α-D-mannopyranosyloxy)cinnamoyl chloride, 3,5-dimethoxy-4-(tetra-O-benzoyl-α-D-mannopyranosyloxy)cinnamoyl bromide, 3,5-dimethoxy-4-(tetra-O-benzoyl-α-D-mannopyranosyloxy)cinnamoyl iodide, 3,5-dimethoxy-4-(6-O-methyl-2,3,4-tribenzyl-β-D-glucuropyranosyloxy)cinnamoyl chloride, 3,5-dimethoxy-4-(6-O-methyl-2,3,4-tribenzyl-β-D-glucuropyranosyloxy) cinnamoyl bromide, 3,5-dimethoxy-4-(6-O-methyl-2,3,4-tribenzyl-β-D-glucuropyranosyloxy)cinnamoyl iodide, 3,5-dimethoxy-4-(tetra-O-benzyl-β-D-glucopyranosyloxy) cinnamoyl chloride, 3,5-dimethoxy-4-(tetra-O-benzyl-β-D-glucopyranosyloxy)cinnamoyl bromide, 3,5-dimethoxy-4-(tetra-O-benzyl-β-D-glucopyranosyloxy)cinnamoyl iodide, 3,5-dimethoxy-4-(tetra-O-benzyl-β-D-galactopyranosyloxy)cinnamoyl chloride, 3,5-dimethoxy-4-(tetra-O-benzyl-β-D-galactopyranosyloxy)cinnamoyl bromide, 3,5-dimethoxy-4-(tetra-O-benzyl-β-D-galactopyranosyloxy)cinnamoyl iodide, 3,5-dimethoxy-4-(tetra-O-benzyl-α-D-mannopyranosyloxy)cinnamoyl chloride, 3,5-dimethoxy-4-(tetra-O-benzyl-α-D-mannopyranosyloxy)cinnamoyl bromide 3,5-dimethoxy-4-(tetra-O-benzyl-α-D-mannopyranosyloxy)cinnamoyl iodide, 3,5-dimethoxy-4-(β-D-glucuropyranosyloxy) cinnamoyl chloride, 3,5-dimethoxy-4-(β-D-glucuropyranosyloxy)cinnamoyl bromide, 3,5-dimethoxy-4-(β-D-glucuropyranosyloxy)cinnamoyl iodide, 3,5-dimethoxy-4-(β-D-glucopyranosyloxy)cinnamoyl chloride, 3,5-dimethoxy-4-(β-D-glucopyranosyloxy)cinnamoyl bromide, 3,5-dimethoxy-4-(β-D-glucopyranosyloxy) cinnamoyl iodide, 3,5-dimethoxy-4-(β-D-galactopyranosyloxy)cinnamoyl chloride, 3,5-dimethoxy-4-(β-D-galactopyranosyloxy)cinnamoyl bromide, 3,5-dimethoxy-4-(β-D-galactopyranosyloxy)cinnamoyl iodide, 3,5-dimethoxy-4-(α-D-mannopyranosyloxy)cinnamoyl chloride, 3,5-dimethoxy-4-(α-D-mannopyranosyloxy) cinnamoyl bromide, 3,5-dimethoxy-4-(α-D-mannopyranosyloxy)cinnamoyl iodide, and physiologically acceptable salts of these compounds are also included in the illustrative example.

Since the glycosyloxyquinolinone derivatives and physiologically acceptable salts of the present invention (to be referred to as "the compound of the present invention" hereinafter) have a function to inhibit both immediate and delayed type allergic reactions and low toxicity as will be described later in examples, they are useful as antiallergic agents for the treatment or prevention of various allergic diseases.

The term "allergic diseases" as used herein means allergic diseases resulting from excess activation of the biological immune mechanism caused by extrinsic or intrinsic antigens, which include immediate type asthma, delayed type asthma, bronchial asthma, pediatric asthma, atopic dermatitis, allergic dermatitis, urticaria, eczema, allergic conjunctivitis, allergic rhinitis, hay fever, food allergy, allergic gastroenteritis, allergic colitis, contact dermatitis, autoimmune disease and the like.

The antiallergic agent which comprises the compound of the present invention as an active ingredient can be administered orally (internal use or inhalation) or parenterally (for example, intravenous injection, subcutaneous injection, percutaneous absorption, rectal administration or the like). Such a pharmaceutical agent can be made into various dosage forms according to the purpose, such as tablets, capsules, granules, fine subtilaes, powders, troches, sublingual tablets, suppositories, ointments, injections, emulsions, suspensions, medicated syrups and the like. These dosage forms can be prepared in accordance with known techniques making use of pharmaceutically acceptable carriers which are commonly used in this type of drugs, such as excipients, bonding agents, disintegrators, lubricants, preservatives, antioxidative agents, isotonic agents, buffering agents, coating agents, sweetening agents, dissolving agents, bases, dispersing agents, stabilizing agents, coloring agents and the like.

Illustrative examples of these pharmaceutically acceptable carriers are listed in the following.

Firstly, as excipients, the following can be listed: starch and derivatives of starch (such as dextrin, carboxymethyl starch and the like), cellulose and derivatives of cellulose (such as methylcellulose, hydroxypropylmethylcellulose and the like), sugars (such as lactose, sucrose, glucose and the like), silicic acid and silicates (such as naturally occurring aluminum silicate, magnesium silicate and the like), carbonates (such as calcium carbonate, magnesium carbonate, sodium hydrogencarbonate and the like), aluminum magnesium hydroxide, synthetic hydrotalcite, polyoxyethylene derivatives, glycerin monostearate, sorbitan monooleic acid and the like.

As bonding agents, the following can be listed: starch and starch derivatives (such as alpha starches, dextrin and the like), cellulose and derivatives of cellulose (such as ethyl cellulose, sodium carboxymethyl cellulose, hydroxypropylmethyl cellulose and the like), gum arabic, traganth, gelatin, sugars (such as glucose, sucrose and the like), ethanol, polyvinyl alcohols and the like.

As disintegrators, the following can be listed: starch and starch derivatives (such as carboxymethyl starch, hydroxypropyl starch and the like), cellulose and cellulose derivatives (such as sodium carboxymethyl cellulose, crystal cellulose, hydroxypropylmethyl cellulose and the like), carbonates (such as calcium carbonate, calcium hydrogencarbonate and the like), traganth, gelatins, agar and the like.

As lubricants, the following can be listed: stearic acid, calcium stearate, magnesium stearate, talc, silicic acid and its salts (such as light silicic anhydrides, naturally occurring aluminum silicates and the like), titanium oxide, calcium hydrogen phosphate, dry aluminum hydroxide gel, macrogol and the like.

As preservatives, the following can be listed: p-hydroxybenzoates, sulfites (such as sodium sulfites, sodium pyrosulfites and the like), phosphates (such as sodium phosphates, calcium polyphosphates, sodium polyphosphates, sodium metaphosphate and the like), alcohols (such as chlorobutanol, benzyl alcohol and the like), benzalkonium chloride, benzethonium chloride, phenol, cresol, chlorocresol, dihydroacetic acid, sodium dihydroacetate, glycerin sorbic acid, sugars and the like.

As anti-oxidative agents, the following can be listed: sulfites (such as sodium sulfite, sodium hydrogen sulfite and the like), rongalite, erythorbic acid, L-ascorbic acid, cysteine, thioglycerol, butylhydroxyanisol, dibutylhydroxytoluene, propylgallic acid, ascorbyl palmitate, dl-a-tocopherol and the like.

As isotonic agents, the following can be listed: sodium chloride, sodium nitrate, potassium nitrate, dextrin, glycerin, glucose and the like.

As buffering agents, the following can be listed: sodium carbonate, hydrochloric acid, boric acid, phosphates (such as sodium hydrogenphosphate) and the like.

As coating agents, the following can be listed: cellulose derivatives (such as hydroxypropyl cellulose, cellulose acetate phthalate, hydroxypropylmethyl cellulose phthalate and the like), shellac, polyvinylpyrrolidone, polyvinylpyridines (such as poly-2-vinylpyridine, poly-2-vinyl-5-ethylpyridine and the like), polyvinylacetyl diethylaminoacetate, polyvinyl alcohol phthalate, methacrylate, methacrylate copolymers and the like.

As sweetening agents, the following can be listed: sugars (such as glucose, sucrose, lactose and the like), sodium saccharin, sugar alcohols and the like.

As dissolving agents, the following can be listed: ethylenediamine, nicotinamide, sodium saccharin, citric acid, citrates, sodium benzoic acid, soaps, polyvinylpyrrolidone, polysolvates, sorbitan fatty acid esters, glycerin, propylene glycol, benzyl alcohols and the like.

As bases, the following can be listed: fats (such as lard and the like), vegetable oils (such as olive oil, sesame oil and the like), animal oil, lanolin acid, petrolatums, paraffin, wax, resins, bentonite, glycerin, glycol oils, higher alcohols (such as stearyl alcohol, cetanol) and the like.

As dispersing agents, the following can be listed: gum arabic, traganth, cellulose derivatives (such as methyl cellulose and the like), stearic acid polyesters, sorbitan sesquioleate, aluminum monostearate, sodium alginate, polysolvates, sorbitan fatty acid esters and the like.

Lastly, as stabilizing agents, the following can be listed: sulfites (such as sodium hydrogen sulfite and the like), nitrogen, carbon dioxide and the like.

Though the content of the compound of the present invention in these pharmaceutical preparations varies depending on the dosage forms, it may be contained preferably in a concentration of from 0.01 to 100% by weight.

Dose of the antiallergic agent of the present invention can be varied over a broad range depending on each warm-blooded animal including human and the like, to be treated, extent of each disease, doctor's judgement and the like. In general, however, it may be administered in a dose of from 0.01 to 50 mg, preferably from 0.01 to 10 mg, as the active ingredient per day per kg body weight in the case of oral administration or in a dose of from 0.01 to 10 mg, preferably from 0.01 to 5 mg, as the active ingredient per day per kg body weight in the case of parenteral administration. The daily dose described above may be used in one portion or in divided portions and changed optionally in accordance with the extent of diseases and doctor's judgement.

The following examples are intended to illustrate this invention, however these examples are intended to illustrate the invention and not to be construed to limit the scope of the invention.

EXAMPLE 1

7-nitro-3-octyloxy-4-(6-O-methyl-2,3,4-triacetyl-β-D-glcuropyranosyloxy)-1-methyl-2(1H)-quinolinone (compound 1)

To a mixture of 46.0 mg of sodium hydride (purity 60%, 1.15 mmol) in 3 ml of N,N-dimethylformamide was added a 400 mg of 7-nitro-3-octyloxy-4-hydroxyl-methyl-2(1H)-quinolinone at room temperature. After the mixture was stirred at 0 to 10° C. for 30 minutes, 454 mg of Methyl 1-bromo-2,3,4-triacetylglucuronate (1.15 mmol) was added. After the mixture was stirred at room temperature for 3 hours, 2 mol/l of aqueous hydrogen chloride solution was added, and extracted with ethyl acetate. The organic layer was washed with water, and concentrated under reduced pressure to give a crude product. Purification of this crude product by column chromatography gave 421 mg of title compound (1). (yield=55%)

$^1$H-NMR (CDCl$_3$, δ-TMS) 8.20(s, 1H), 8.09(s, 2H), 5.84 (d, 1H, J=7.2 Hz), 5.41~5.28(m, 3H), 4.21(t, 2H, J=7.2 Hz), 4.08(d, 1H, J=9.2 Hz), 3.78(s, 3H), 1.80~1.29(m, 12H), 0.88(t, 3H, J=6.8 Hz)

IR (KBr, cm$^{-1}$): 2850, 1740, 1550, 1345

Elemental analysis for: $C_{31}H_{40}N_2O_{14}$

Calculated (%): C, 56.02; H, 6.07; N, 4.21; O, 33.70.

Found (%): C, 55.95; H, 6.03; N, 4.26; O, 33.79.

EXAMPLE 2

7-nitro-3-octyloxy-4-(6-O-methyl-2,3,4-triacetyl-β-D-glcuropyranosyloxy)-1-methyl-2(1H)-quinolinone (compound 1)

In accordance with EXAMPLE 1, DBU(1,8-Diazabicyclo [5,4,0]undec-7-ene was used instead of sodium hydride, the title compound (1) was obtained.

EXAMPLE 3

7-nitro-3-octyloxy-4-(6-O-methyl-2,3,4-triacetyl-β-D-glcuropyranosyloxy)-1-methyl-2(1H)-quinolinone (compound 1)

In accordance with EXAMPLE 1, calcium hydride was used instead of sodium hydride, the title compound (1) was obtained.

EXAMPLE 4

7-amino-3-octyloxy-4-(6-O-methyl-2,3,4-triacetyl-β-D-glcuropyranosyloxy)-1-methyl-2(1H)-quinolinone (compound 2)

A mixture of 400 mg of 7-nitro-3-octyloxy-4-(6-O-methyl-2,3,4-triacetyl-β-D-glcuropyranosyloxy)-1-methyl-2(1H)-quinolinone (0.60 mmol) and 40 mg of 10% palladium carbon in 4 ml of ethyl acetate was stirred under hydrogen gas at room temperature for 3 hours. After hydrogen gas was replaced by nitrogen gas, the mixture was filtrated and the filtrate was concentrated under reduced pressure. The resulting crude product was crystallized from diethyl ether to give 298 mg of title compound (2). (yield=78%)

$^1$H-NMR (CDCl$_3$, δ-TMS) 7.67(d, 1H, J=8.4 Hz), 6.62(m, 1H), 6.49(s, 1H), 5.87(d, 1H, J=7.6 Hz) 5.37~5.30(m, 3H), 4.11~4.05(m, 3H), 3.69(s, 3H), 3.62(s, 3H), 2.03(s, 6H), 1.80~1.18(m, 12H), 0.88(t, 3H, J=6.8 Hz)

IR (KBr, cm$^{-1}$): 3350, 2850, 1740, 1550, 1220

Elemental analysis for: $C_{31}H_{42}N_2O_{12}$

Calculated (%): C, 58.67; H, 6.67; N, 4.41; O, 30.25.

Found (%): C, 58.56; H, 6.63; N, 4.46; O, 30.35.

EXAMPLE 5

7-amino-3-octyloxy-4-(tetra-O-acetyl-β-D-glucopyranosyloxy)-1-methyl-2(1H)-quinolinone (compound 3)

In accordance with EXAMPLE 1 and 4, tetra-O-acetyl-β-D-glucopyranosyl bromide was used instead of Methyl1-bromo-2,3,4-triacetylglucuronate, the title compound (3) was obtained.

$^1$H-NMR (CDCl$_3$, δ-TMS) 7.70(d, 1H, J=8.4 Hz), 6.62(m, 1H), 6.49(s, 1H), 5.70(d, 1H, J=7.6 Hz) 5.45~5.30(m, 2H), 5.12~5.07(m, 1H), 4.20~4.05(m, 5H), 3.62(s, 3H), 2.18(s, 3H), 2.14(s, 3H), 1.80~1.18(m, 12H), 0.88(t, 3H, J=6.8 Hz)

IR (KBr, cm$^{-1}$): 3350, 2850, 1725, 1225

Elemental analysis for: $C_{32}H_{44}N_2O_{12}$

Calculated (%): C, 59.25; H, 6.84; N, 4.32; O, 29.60.

Found (%): C, 59.32; H, 6.73; N, 4.46; O, 29.49.

EXAMPLE 6

7-amino-3-octyloxy-4-(tetra-O-acetyl-β-D-galactopyranosyloxy)-1-methyl-2(1H)-quinolinone (compound 4)

In accordance with EXAMPLE 1 and 4, tetra-O-acetyl-β-D-galactopyranosyl bromide was used instead of Methyl1-bromo-2,3,4-triacetylglucuronate, the title compound (4) was obtained.

$^1$H-NMR (CDCl$_3$, δ-TMS) 7.72(d, 1H, J=8.4 Hz), 6.62(m, 1H), 6.49(s, 1H), 5.70(d, 1H, J=7.6 Hz), 5.45~5.30(m, 2H), 5.07~5.06(m, 1H), 4.18~4.05(m, 5H), 3.62(s, 3H), 2.18(s, 3H), 2.14(s, 3H), 2.05(s, 3H), 1.80~1.18(m, 12H), 0.88(t, 3H, J=6.8 Hz)

IR (KBr, cm$^{-1}$): 3350, 2850, 1725, 1225

Elemental analysis for: $C_{32}H_{44}N_2O_{12}$

Calculated (%): C, 59.25; H, 6.84; N, 4.32; O, 29.60.

Found (%): C, 59.34; H, 6.83; N, 4.36; O, 29.47

EXAMPLE 7

7-amino-3-octyloxy-4-(tetra-O-acetyl-α-D-mannopyranosyloxy)-1-methyl-2(1H)-quinolinone (compound 5)

In accordance with EXAMPLE 1 and 4, tetra-O-acetyl-α-D-mannopyranosyl bromide was used instead of Methyl1-bromo-2,3,4-triacetylglucuronate, the title compound (5) was obtained.

$^1$H-NMR (CDCl$_3$, δ-TMS) 7.72(d, 1H, J=8.4 Hz), 6.62(m, 1H), 6.49(s, 1H), 5.70(d, 1H, J=7.6 Hz), 5.45~5.30(m, 2H), 5.07~5.06(m, 1H), 4.18~4.05(m, 5H), 3.62(s, 3H), 2.18(s, 3H), 2.14(s, 3H), 2.05(s, 6H), 1.80~1.18(m, 12H), 0.88(t, 3H, J=6.8 Hz)

IR (KBr, cm$^{-1}$): 3350, 2850, 1725, 1225

Elemental analysis for: $C_{32}H_{44}N_2O_{12}$

Calculated (%): C, 59.25; H, 6.84; N, 4.32; O, 29.60.

Found (%): C, 59.29; H, 6.78; N, 4.35; O, 29.58.

EXAMPLE 8

7-amino-3-octyloxy-4-(6-O-methyl-2,3,4-tribenzoyl-β-D-glcuropyranosyloxy)-1-methyl-2(1H)-quinolinone (compound 6)

In accordance with EXAMPLE 1 and 4, Methyl1-bromo-2,3,4-tribenzoylglucuronate was used instead of Methyl 1-bromo-2,3,4-triacetylglucuronate, the title compound (6) was obtained.

$^1$H-NMR (CDCl$_3$, δ-TMS) 7.85~7.23(m, 16H), 6.62(m, 1H), 6.49(s, 1H), 5.87(d, 1H, J=7.6 Hz), 5.37~5.30(m, 3H), 4.11~4.05(m, 3H), 3.69(s, 3H), 3.62(s, 3H), 1.80~1.18(m, 12H), 0.88(t, 3H, J=6.8 Hz)

IR (KBr, cm$^{-1}$): 3350, 2850, 1740, 1220

Elemental analysis for: $C_{46}H_{48}N_2O_{12}$

Calculated (%): C, 67.31; H, 5.89; N, 3.41; O, 23.39.

Found (%): C, 67.28; H, 5.73; N, 3.46; O, 23.53.

EXAMPLE 9

7-amino-3-octyloxy-4-(β-D-glcuropyranosyloxy)-1-methyl-2(1H)-quinolinone (compound 7)

To the solution of 400 mg of 7-amino-3-octyloxy-4-(6-O-methyl-2,3,4-triacetyl-β-D-glcuropyranosyloxy)-1-methyl-2(1H)-quinolinone (0.63 mmol) in 4 ml of methanol was added 54 mg of sodium methoxide(1.00 mmol) in 1 ml of methanol with cooling on ice bath. After stirring at room temperature for 2 hours, to the solution was added 1.0 g of Amberlyst-15 and stirred at room temperature for 2 hours. The reaction mixture was filtered, the filtrate was concentrated under reduced pressure. The resulting crude product was crystallized from tetrahydrofuran and hexane to give 255 mg of title compound (7). (yield=82%)

$^1$H-NMR (d$_6$-DMSO, δ-TMS) 10.67(bs, 1H), 7.67(d, 1H, J=8.4 Hz), 6.62(m, 1H), 6.49(s, 1H), 5.87(d, 1H, J=7.6 Hz), 5.68(s, 2H), 4.80(s, 3H), 4.12(t, 2H, J=7.2 Hz), 3.90~3.20 (m, 4H), 3.69(s, 3H), 1.80~1.18(m, 12H), 0.88(t, 3H, J=6.8 Hz)

IR (KBr, cm$^{-1}$): 3350, 2850, 1740, 1220

Elemental analysis for: $C_{24}H_{34}N_2O_9$

Calculated (%): C, 58.29; H, 6.93; N, 5.66; O, 29.12.

Found (%): C, 58.34; H, 6.93; N, 5.56; O, 29.17.

EXAMPLE 10

7-amino-3-octyloxy-4-(β-D-glucopyranosyloxy)-1-methyl-2(1H)-quinolinone (compound 8)

In accordance with EXAMPLE 9, 7-amino-3-octyloxy-4-(tetra-O-acetyl-β-D-glucopyranosyloxy)-1-methyl-2(1H)-quinolinone was used instead of 7-amino-3-octyloxy-4-(6-O-methyl-2,3,4-triacetyl-β-D-glcuropyranosyloxy)-1-methyl-2(1H)-quinolinone, the title compound (8) was obtained.

¹H-NMR (d₆-DMSO, δ-TMS) 7.67(d, 1H, J=8.4 Hz), 6.62(m,1H), 6.49(s, 1H), 5.87(d, 1H, J=7.6 Hz), 5.68(s, 2H), 4.80(s, 3H), 4.65(d, 1H, J=7.6 Hz), 4.12(t, 2H, J=7.2 Hz), 3.90~3.20(m, 6H), 3.69(s, 3H), 1.80~1.18(m, 12H), 0.88(t, 3H, J=6.8 Hz)

IR (KBr, cm⁻¹): 3350, 2850, 1740, 1220

Elemental analysis for: $C_{24}H_{36}N_2O_8$

Calculated (%): C, 59.99; H, 7.55; N, 5.83; O, 26.63.

Found (%): C, 59.93; H, 7.45; N, 5.76; O, 26.86.

EXAMPLE 11

7-amino-3-octyloxy-4-(β-D-galactopyranosyloxy)-1-methyl-2(1H)-quinolinone (compound 9)

In accordance with EXAMPLE 9, 7-amino-3-octyloxy-4-(tetra-O-acetyl-β-D-galactopyranosyloxy)-1-methyl-2(1H)-quinolinone was used instead of 7-amino-3-octyloxy-4-(6-O-methyl-2,3,4-triacetyl-β-D-glcuropyranosyloxy)-1-methyl-2(1H)-quinolinone, the title compound (9) was obtained.

¹H-NMR (d₆-DMSO, δ-TMS) 7.67(d, 1H, J=8.4 Hz), 6.62(m, 1H), 6.49(s, 1H), 5.87(d, 1H, J=7.6 Hz), 5.68(s, 2H), 4.80(s, 3H), 4.65(d, 1H, J=7.6 Hz), 4.12(t, 2H, J=7.2 Hz), 3.90~3.20(m, 6H), 3.69(s, 3H), 1.80~1.18(m, 12H), 0.88(t, 3H, J=6.8 Hz)

IR (KBr, cm⁻¹): 3350, 2850, 1740, 1220

Elemental analysis for: $C_{24}H_{36}N_2O_8$

Calculated (%): C, 59.99; H, 7.55; N, 5.83; O, 26.63.

Found (%): C, 59.89; H, 7.56; N, 5.87; O, 26.68.

EXAMPLE 12

7-amino-3-octyloxy-4-(α-D-mannopyranosyloxy)-1-methyl-2(1H)-quinolinone (compound 10)

In accordance with EXAMPLE 9, 7-amino-3-octyloxy-4-(tetra-O-acetyl-α-D-mannopyranosyloxy)-1-methyl-2(1H)-quinolinone was used instead of 7-amino-3-octyloxy-4-(6-O-methyl-2,3,4-triacetyl-β-D-glcuropyranosyloxy)-1-methyl-2(1H)-quinolinone, the title compound (10) was obtained.

¹H-NMR (d₆-DMSO, δ-TMS) 7.67(d, 1H, J=8.4 Hz), 6.62(m, 1H), 6.49(s, 1H), 5.87(d, 1H, J=7.6 Hz), 5.68(s, 2H), 4.80(s, 3H), 4.65(d, 1H, J=7.6 Hz), 4.12(t, 2H, J=7.2 Hz), 3.90~3.20(m, 6H), 3.69(s, 3H), 1.80~1.18(m, 12H), 0.88(t, 3H, J=6.8 Hz)

IR (KBr, cm⁻¹): 3350, 2850, 1740, 1220

Elemental analysis for: $C_{24}H_{36}N_2O_8$

Calculated (%): C, 59.99; H, 7.55; N, 5.83; O, 26.63.

Found (%): C, 60.02; H, 7.45; N, 5.79; O, 26.74.

EXAMPLE 13

7-[3,5-dimethoxy-4-(6-O-methyl-2,3,4-triacetyl-β-D-glcuropyranosyloxy)cinnamoyl]amino-3-octyloxy-4-(6-O-methyl-2,3,4-triacetyl-β-D-glcuropyranosyloxy)-1-methyl-2(1H)-quinolinone (compound 11)

To the solution of 300 mg of 3,5-dimethoxy-4-(6-O-methyl-2,3,4-triacetyl-β-D-glcuropyranosyloxy)cinnamic acid (0.555 mmol) in 2 ml of tetrahydrofuran was added 4 mg of N, N-dimethylformamide. After the solution was stirred at room temperature, 348 mg of thionyl chloride was added. After stirring at room temperature for 1 hours, to the solution was added 387 mg of 7-amino-3-octyloxy-4-(6-O-methyl-2,3,4-triacetyl-β-D-glcuropyranosyloxy)-1-methyl-2(1H)-quinolinone in 3 ml of tetrahydrofuran and 214 mg of pyridine. After the mixture was stirred at room temperature for 30 minutes, 20 ml of water was added, and extracted with 30 ml of ethyl acetate. The organic layer was washed with water, and concentrated under reduced pressure to give a crude product. Purification of this crude product by column chromatography on silica gel gave 584 mg of title compound (11). (yield=91%)

¹H-NMR (CDCl₃, δ-TMS) 8.30(s, 1H), 8.01(d, 1H, J=8.0 Hz), 7.83(d, 1H, J=8.4 Hz), 7.64(d, 1H, J=15.2 Hz), 7.08(m, 1H), 6.73(s, 2H), 6.51(d, 1H, J=15.2 Hz), 5.89(d, 1H, J=7.6 Hz), 5.52(m, 1H), 5.32(m, 7H), 4.09(m, 3H), 3.84(s, 6H), 3.71(s, 6H), 3.67(s, 3H), 2.04(m, 18H), 1.40~1.20(m, 12H), 0.88(m, 3H)

IR (KBr, cm⁻¹): 3350, 1745, 1680, 1220

Elemental analysis for: $C_{55}H_{68}N_2O_{25}$

Calculated (%): C, 57.09; H, 5.92; N, 2.42; O, 34.57.

Found (%): C, 57.12; H, 5.89; N, 2.39; O, 34.60.

EXAMPLE 14

7-[3,5-dimethoxy-4-(6-O-methyl-2,3,4-triacetyl-β-D-glcuropyranosyloxy)cinnamoyl]amino-3-octyloxy-4-hydroxy-1-methyl-2(1H)-quinolinone (compound 12)

In accordance with EXAMPLE 13, 7-amino-3-octyloxy-4-(6-O-methyl-2,3,4-triacetyl-β-D-glucopyranosyloxy)-1-methyl-2(1H)-quinolinone was used instead of 7-amino-3-octyloxy-4-(6-O-methyl-2,3,4-triacetyl-β-D-glcuropyranosyloxy)-1-methyl-2(1H)-quinolinone, the title compound (12) was obtained.

¹H-NMR (CDCl₃, δ-TMS) 8.30(s, 1H), 8.01(d, 1H, J=8.0 Hz), 7.83(d, 1H, J=8.4 Hz), 7.64(d, 1H, J=15.2 Hz), 7.08(m, 1H), 6.73(s, 2H), 6.51(d, 1H, J=15.2 Hz), 5.52(m, 1H), 5.35(m, 5H), 4.09(m, 2H), 3.84(s, 6H), 3.71(s, 3H), 3.67(s, 3H), 2.04(m, 9H), 1.40~1.20(m, 12H) 0.88(m, 3H)

IR (KBr, cm⁻¹): 3350, 1745, 1680, 1220

Elemental analysis for : $C_{42}H_{52}N_2O_{16}$

Calculated (%): C, 59.99; H, 6.23; N, 3.33; O, 30.44.

Found (%): C, 60.01; H, 6.35; N, 3.37; O, 30.27.

EXAMPLE 15

7-(3,5-dimethoxy-4-hydroxycinnamoyl)amino-3-octyloxy-4-(6-O-methyl-2,3,4-triacetyl-β-D-glcuropyranosyloxy)-1-methyl-2(1H)-quinolinone (compound 13)

In accordance with EXAMPLE 13, 3,5-dimethoxy-4-hydroxycinnamic acid was used instead of 7-amino-3-octyloxy-4-(6-O-methyl-2,3,4-triacetyl-β-D-glcuropyranosyloxy)-1-methyl-2(1H)-quinolinone, the title compound (13) was obtained.

¹H-NMR (CDCl₃, δ-TMS) 8.30(s, 1H), 8.01(d, 1H, J=8.0 Hz), 7.83(d, 1H, J=8.4 Hz), 7.64(d, 1H, J=15.2 Hz), 7.05(m, 1H), 6.73(s, 2H), 6.51(d, 1H, J=15.2 Hz), 5.90(d, 1H, J=7.6 Hz), 5.35(m, 5H), 4.09(m, 2H), 3.84(s, 6H), 3.71(s, 3H), 3.67(s, 3H), 2.04(m, 9H), 1.40~1.20(m, 12H) 0.88(m, 3H)

IR (KBr, cm⁻¹): 3350, 1745, 1680, 1250

Elemental analysis for: $C_{42}H_{52}N_2O_{16}$

Calculated (%): C, 59.99; H, 6.23; N, 3.33; O, 30.44.

Found (%): C, 60.00; H, 6.28; N, 3.29; O, 30.43.

EXAMPLE 16

7-[3,5-dimethoxy-4-(β-D-glucuropyranosyloxy)cinnamoyl]amino-3-octyloxy-4-(β-D-glucuropyranosyloxy))-1-methyl-2(1H)-quinolinone (compound 14)

In accordance with EXAMPLE 9, 7-[3,5-dimethoxy-4-(6-O-methyl-2,3,4-triacetyl-β-D-glcuropyranosyloxy)

cinnamoyl]amino-3-octyloxy-4-(6-O-methyl-2,3,4-triacetyl-β-D-glcuropyranosyloxy)-1-methyl-2(1H)-quinolinone was used instead of 7-amino-3-octyloxy-4-(6-O-methyl-2,3,4-triacetyl-β-D-glcuropyranosyloxy)-1-methyl-2(1H)-quinolinone, the title compound (14) was obtained.

$^1$H-NMR (d$_6$-DMSO, δ-TMS) 11.05(s, 1H), 8.12(s, 1H), 7.86(d, 1H, J=8.8 Hz), 7.46(m, 3H), 7.02(m, 3H), 6.80(s, 1H), 6.60(s, 1H), 5.52~4.99(m, 6H), 4.09(m, 1H), 3.95(m, 1H), 3.84(s, 6H), 3.55(s, 3H), 3.27~3.17(m, 9H), 1.65~1.15 (m, 12H), 0.86(m, 3H)

IR (KBr, cm$^{-1}$): 3350, 1680, 1220

Elemental analysis for: C$_{41}$H$_{52}$N$_2$O$_{19}$

Calculated (%): C, 56.16; H, 5.98; N, 3.19; O, 34.67.

Found (%): C, 56.12; H, 5.99; N, 3.23; O, 34.66.

EXAMPLE 17

7-[3,5-dimethoxy-4-(β-D-glucuropyranosyloxy) cinnamoyl]amino-3-octyloxy-4-hydroxy-1-methyl-2 (1H)-quinolinone (compound 15)

In accordance with EXAMPLE 9, 7-[3,5-dimethoxy-4-(6-O-methyl-2,3,4-triacetyl-β-D-glcuropyranosyloxy) cinnamoyl]amino-3-octyloxy-4-hydroxy-1-methyl-2(1H)-quinolinone was used instead of 7-amino-3-octyloxy-4-(6-O-methyl-2,3,4-triacetyl-β-D-glcuropyranosyloxy)-1-methyl-2(1H)-quinolinone, the title compound (15) was obtained.

$^1$H-NMR (d$_6$-DMSO, δ-TMS) 10.68(s, 1H), 8.02(s, 1H), 7.84(d, 1H, J=8.8 Hz), 7.55(m, 3H), 6.99(m, 3H), 6.87(d, 1H, J=15.6 Hz), 5.09(s, 2H), 5.07(m, 1H), 3.96(d, 1H, J=7.2 Hz), 3.84(s, 6H), 3.56(s, 3H), 3.42~3.18(m, 5H), 1.72~1.15 (m, 12H), 0.86(m, 3H)

IR (KBr, cm$^{-1}$): 3350, 1680, 1220

Elemental analysis for: C$_{35}$H$_{44}$N$_2$O$_{13}$

Calculated (%): C, 59.99; H, 6.33; N, 4.00; O, 29.68.

Found (%): C, 60.02; H, 6.35; N, 3.96; O, 29.67.

EXAMPLE 18

7-(3,5-dimethoxy-4-hydroxycinnamoyl)amino-3-octyloxy-4-(β-D-glcuropyranosyloxy)-1-methyl-2 (1H)-quinolinone (compound 16)

In accordance with EXAMPLE 9, 7-(3,5-dimethoxy-4-hydroxycinnamoyl)amino-3-octyloxy-4-(6-O-methyl-2,3,4-triacetyl-β-D-glcuropyranosyloxy)-1-methyl-2(1H)-quinolinone was used instead of 7-amino-3-octyloxy-4-(6-O-methyl-2,3,4-triacetyl-β-D-glcuropyranosyloxy)-1-methyl-2(1H)-quinolinone, the title compound (16) was obtained.

$^1$H-NMR (d$_6$-DMSO, δ-TMS) 10.27(s, 1H), 8.08(s, 1H), 7.90(d, 1H, J=8.8 Hz), 7.44(m, 2H), 7.30(s, 1H), 6.79(s, 2H), 6.45(d, 1H, J=15.6 Hz), 5.48(d, 1H, J=7.6 Hz), 5.32(s, 1H), 5.00(s, 1H), 4.10(m, 1H), 3.99(m, 1H), 3.75(s, 6H), 3.58(s, 3H), 3.30~3.10(m, 6H), 1.72~1.20(m, 12H), 0.87(m, 3H)

IR (KBr, cm$^{-1}$): 3350, 1680, 1220

Elemental analysis for: C$_{35}$H$_{44}$N$_2$O$_{13}$

Calculated (%): C, 59.99; H, 6.33; N, 4.00; O, 29.68.

Found (%): C, 59.88; H, 6.23; N, 4.03; O, 29.86.

EXAMPLE 19

7-[3,5-dimethoxy-4-(tetra-O-acetyl-β-D-glucopyranosyloxy)cinnamoyl]amino-3-octyloxy-4-(tetra-O-acetyl-β-D-glucopyranosyloxy)-1-methyl-2 (1H)-quinolinone (compound 17)

In accordance with EXAMPLE 13, 7-amino-3-octyloxy-4-(tetra-O-acetyl-β-D-glucopyranosyloxy)-1-methyl-2(1H)-quinolinone and 3,5-dimethoxy-4-(tetra-O-acetyl-β-D-glucopyranosyloxy)cinnamic acid were used instead of 7-amino-3-octyloxy-4-(6-O-methyl-2,3,4-triacetyl-β-D-glcuropyranosyloxy)-1-methyl-2(1H)-quinolinone and 3,5-dimethoxy-4-(6-O-methyl-2,3,4-triacetyl-β-D-glcuropyranosyloxy)cinnamic acid, the title compound (17) was obtained.

$^1$H-NMR (CDCl$_3$, δ-TMS) 8.28(s, 1H), 8.01(d, 1H, J=8.0 Hz), 7.83(d, 1H, J=8.4 Hz), 7.64(d, 1H, J=15.2 Hz), 7.08(m, 1H), 6.73(s, 2H), 6.51(d, 1H, J=15.2 Hz), 5.78(d, 1H, J=7.6 Hz), 5.49(m, 1H), 5.32(m, 7H), 4.10(m, 7H), 3.84(s, 6H), 3.71(s, 6H), 3.67(s, 3H), 2.04(m, 18H), 1.40~1.20(m, 12H), 0.87(m, 3H)

IR (KBr, cm$^{-1}$): 3350, 1745, 1680

Elemental analysis for: C$_{57}$H$_{72}$N$_2$O$_{25}$

Calculated (%): C, 57.77; H, 6.12; N, 2.36; O, 33.75.

Found (%): C, 57.68; H, 6.09; N, 2.46; O, 33.77.

EXAMPLE 20

7-[3,5-dimethoxy-4-(tetra-O-acetyl-β-D-glucopyranosyloxy)cinnamoyl]amino-3-octyloxy-4-hydroxy-1-methyl-2(1H)-quinolinone (compound 18)

In accordance with EXAMPLE 19, 7-amino-3-octyloxy-4-hydroxyl-methyl-2(1H)-quinolinone was used instead of 7-amino-3-octyloxy-4-(6-O-methyl-2,3,4-triacetyl-β-D-glcuropyranosyloxy)-1-methyl-2(1H)-quinolinone, the title compound (18) was obtained.

$^1$H-NMR (CDCl$_3$, δ-TMS) 8.30(s, 1H), 8.05(d, 1H, J=8.0 Hz), 7.83(d, 1H, J=8.4 Hz), 7.64(d, 1H, J=15.2 Hz), 7.08(m, 1H), 6.73(s, 2H), 6.51(d, 1H, J=15.2 Hz), 5.52(m, 1H), 5.35(m, 5H), 4.15(m, 4H), 3.84(s, 6H), 3.71(s, 3H), 3.67(s, 3H), 2.04(m, 9H), 1.40~1.20(m, 12H) 0.88(m, 3H)

IR (KBr, cm$^{-1}$): 3350, 1745, 1680, 1220

Elemental analysis for: C$_{43}$H$_{54}$N$_2$O$_{16}$

Calculated (%): C, 60.41; H, 6.37; N, 3.28; O, 29.94.

Found (%): C, 60.29; H, 6.35; N, 3.19; O, 30.17.

EXAMPLE 21

7-(3,5-dimethoxy-4-hydroxycinnamoyl)amino-3-octyloxy-4-(tetra-O-acetyl-β-D-glucopyranosyloxy)-1-methyl-2(1H)-quinolinone (compound 19)

In accordance with EXAMPLE 19, 3,5-dimethoxy-4-hydroxycinnamic acid was used instead of 3,5-dimethoxy-4-(tetra-O-acetyl-β-D-glucopyranosyloxy)cinnamic acid, the title compound (19) was obtained.

$^1$H-NMR (CDCl$_3$, δ-TMS) 8.30(s, 1H), 8.01(d, 1H, J=8.0 Hz), 7.83(d, 1H, J=8.4 Hz), 7.64(d, 1H, J=15.2 Hz), 7.05(m, 1H), 6.73(s, 2H), 6.51(d, 1H, J=15.2 Hz), 5.90(d, 1H, J=7.6 Hz), 5.35(m, 5H), 4.15(m, 4H), 3.84(s, 6H), 3.84(s, 6H), 3.71(s, 3H), 3.67(s, 3H), 2.04(m, 9H), 1.40~1.20(m, 12H), 0.88(m, 3H)

IR (KBr, cm$^{-1}$): 3350, 1745, 1680, 1250

Elemental analysis for: C$_{43}$H$_{54}$N$_2$O$_{16}$

Calculated (%): C, 60.41; H, 6.37; N, 3.28; O, 29.94.

Found (%): C, 60.23; H, 6.29; N, 3.35; O, 30.13.

EXAMPLE 22

7-[3,5-dimethoxy-4-(β-D-glucopyranosyloxy) cinnamoyl]amino-3-octyloxy-4-(β-D-glucopyranosyloxy)-1-methyl-2(1H)-quinolinone (compound 20)

In accordance with EXAMPLE 16, 7-[3,5-dimethoxy-4-(tetra-O-acetyl-β-D-glucopyranosyloxy)cinnamoyl]amino- 3-octyloxy-4-(tetra-O-acetyl-β-D-glucopyranosyloxy)-1-methyl-2(1H)-quinolinone was used instead of 7-[3,5-dimethoxy-4-(6-O-methyl-2,3,4-triacetyl-β-D-glcuropyranosyloxy)cinnamoyl]amino-3-octyloxy-4-(6-O-methyl-2,3,4-triacetyl-β-D-glcuropyranosyloxy)-1-methyl-2(1H)-quinolinone, the title compound (20) was obtained.

$^1$H-NMR (d$_6$-DMSO, δ-TMS) 11.05(s, 1H), 8.12(s, 1H), 7.86(d, 1H, J=8.8 Hz), 7.46(m, 3H), 7.02(m, 3H), 6.80(s, 1H), 6.60(s, 1H), 5.52~4.99(m, 6H), 4.11(m, 5H), 3.95(m, 1H), 3.84(s, 6H), 3.55(s, 3H), 3.27~3.17(m, 9H), 1.65~1.15 (m, 12H), 0.86(m, 3H)

IR (KBr, cm$^{-1}$): 3350, 1680, 1220

Elemental analysis for: $C_{41}H_{56}N_2O_{17}$

Calculated (%): C, 58.01; H, 6.65; N, 3.30; O, 32.04.

Found (%): C, 58.11; H, 6.78; N, 3.31; O, 31.80.

EXAMPLE 23

7-[3,5-dimethoxy-4-(β-D-glucopyranosyloxy)cinnamoyl]amino-3-octyloxy-4-hydroxy-1-methyl-2(1H)-quinolinone (compound 21)

In accordance with EXAMPLE 16, 7-[3,5-dimethoxy-4-(tetra-O-acetyl-β-D-glucopyranosyloxy)cinnamoyl]amino-3-octyloxy-4-hydroxy-1-methyl-2(1H)-quinolinone was used instead of 7-[3,5-dimethoxy-4-(6-O-methyl-2,3,4-triacetyl-β-D-glcuropyranosyloxy)cinnamoyl]amino-3-octyloxy-4-(6-O-methyl-2,3,4-triacetyl-β-D-glcuropyranosyloxy)-1-methyl-2(1H)-quinolinone, the title compound (21) was obtained.

$^1$H-NMR (d$_6$-DMSO, δ-TMS) 10.75(s, 1H), 8.02(s, 1H), 7.84(d, 1H, J=8.8 Hz), 7.55(m, 3H), 6.99(m, 3H), 6.87(d, 1H, J=15.6 Hz), 5.09(s, 2H), 5.07(m, 1H), 4.10(m, 2H), 3.96(t, 2H, J=7.2 Hz), 3.84(s, 6H), 3.56(s, 3H), 3.42~3.18 (m, 5H), 1.72~1.15(m, 12H), 0.86(m, 3H)

IR (KBr, cm$^{-1}$): 3350, 1680, 1220

Elemental analysis for: $C_{35}H_{46}N_2O_{12}$

Calculated (%): C, 61.21; H, 6.75; N, 4.08; O, 27.96.

Found (%): C, 61.12; H, 6.65; N, 3.96; O, 28.27.

EXAMPLE 24

7-(3,5-dimethoxy-4-hydroxycinnamoyl)amino-3-octyloxy-4-(β-D-glucopyranosyloxy)-1-methyl-2(1H)-quinolinone (compound 22)

In accordance with EXAMPLE 16, 7-[3,5-dimethoxy-4-hydroxycinnamoyl]amino-3-octyloxy-4-(tetra-O-acetyl-β-D-glucopyranosyloxy)-1-methyl-2(1H)-quinolinone was used instead of 7-[3,5-dimethoxy-4-(6-O-methyl-2,3,4-triacetyl-β-D-glcuropyranosyloxy)cinnamoyl]amino-3-octyloxy-4-(6-)-methyl-2,3,4-triacetyl-β-D-glcuropyranosyloxy)-1-methyl-2(1H)-quinolinone, the title compound (22) was obtained.

$^1$H-NMR (d$_6$-DMSO, β-TMS) 10.27(s, 1H), 8.08(s, 1H), 7.90(d, 1H, J=8.8 Hz), 7.44(m, 2H), 7.30(s, 1H), 6.79(s, 2H), 6.45(d, 1H, J=15.6 Hz), 5.48(d, 1H, J=7.6 Hz), 5.32(s, 1H), 5.00(s, 1H), 4.16(m, 3H), 3.99(m, 1H), 3.75(s, 6H), 3.58(s, 3H), 3.30~3.10(m, 6H), 1.72~1.20(m, 12H), 0.87(m, 3H)

IR (KBr, cm$^{-1}$): 3350, 1680, 1220

Elemental analysis for: $C_{35}H_{46}N_2O_{12}$

Calculated (%): C, 61.21; H, 6.75; N, 4.08; O, 27.96.

Found (%): C, 61.24; H, 6.77; N, 4.06; O, 27.93.

EXAMPLE 25

7-[3,5-dimethoxy-4-(tetra-O-acetyl-β-D-galactopyranosyloxy)cinnamoyl]amino-3-octyloxy-4-(β-D-galactopyranosyloxy)-1-methyl-2(1H)-quinolinone (compound 23)

In accordance with EXAMPLE 13, 7-amino-3-octyloxy-4-(tetra-O-acetyl-β-D-galactopyranosyloxy)-1-methyl-2(1H)-quinolinone and 3,5-dimethoxy-4-(tetra-O-acetyl-β-D-galactopyranosyloxy)cinnamic acid were used instead of 7-amino-3-octyloxy-4-(6-O-methyl-2,3,4-triacetyl-β-D-glcuropyranosyloxy)-1-methyl-2(1H)-quinolinone and 3,5-dimethoxy-4-(6-O-methyl-2,3,4-triacetyl-β-D-glcuropyranosyloxy)cinnamic acid, the title compound (23) was obtained.

$^1$H-NMR (CDCl$_3$, δ-TMS) 8.28(s, 1H), 8.01(d, 1H, J=8.0 Hz), 7.83(d, 1H, J=8.4 Hz), 7.64(d, 1H, J15.2 Hz), 7.08(m, 1H), 6.73(s, 2H), 6.51(d, 1H, J=15.2 Hz), 5.78(d, 1H, J=7.6 Hz), 5.49(m, 1H), 5.32(m, 7H), 4.10(m, 7H), 3.84(s, 6H), 3.71(s, 6H), 3.67(s, 3H), 2.04(m, 18H), 1.40~1.20(m, 12H), 0.87(m, 3H)

IR (KBr, cm$^{-1}$): 3350, 1745, 1680

Elemental analysis for: $C_{57}H_{72}N_2O_{25}$

Calculated (%): C, 57.77; H, 6.12; N, 2.36; O, 33.75.

Found (%): C, 57.69; H, 6.11; N, 2.42; O, 33.78.

EXAMPLE 26

7-[3,5-dimethoxy-4-(tetra-O-acetyl-β-D-galactopyranosyloxy)cinnamoyl]amino-3-octyloxy-4-hydroxy-1-methyl-2(1H)-quinolinone (compound 24)

In accordance with EXAMPLE 13, 7-amino-3-octyloxy-4-hydroxy-1-methyl-2(1H)-quinolinone and 3,5-dimethoxy-4-(tetra-O-acetyl-β-D-galactopyranosyloxy)cinnamic acid were used instead of 7-amino-3-octyloxy-4-(6-O-methyl-2,3,4-triacetyl-β-D-glcuropyranosyloxy)-1-methyl-2(1H)-quinolinone and 3,5-dimethoxy-4-(6-O-methyl-2,3,4-triacetyl-β-D-glcuropyranosyloxy)cinnamic acid, the title compound (24) was obtained.

$^1$H-NMR (CDCl$_3$, δ-TMS) 8.37(s, 1H), 8.05(d, 1H, J=8.0 Hz), 7.83(d, 1H, J=8.4 Hz), 7.64(d, 1H, J=15.2 Hz), 7.08(m, 1H), 6.72(s, 2H), 6.51(d, 1H, J=15.2 Hz), 5.52(m, 1H), 5.35(m, 5H), 4.15(m, 4H), 3.84(s, 6H), 3.71(s, 3H), 3.67(s, 3H), 2.04(m, 9H), 1.40~1.20(m, 12H), 0.88(m, 3H)

IR (KBr, cm$^{-1}$): 3350, 1745, 1680, 1220

Elemental analysis for: $C_{43}H_{54}N_2O_{16}$

Calculated (%): C, 60.41; H, 6.37; N, 3.28; O, 29.94.

Found (%): C, 60.29; H, 6.35; N, 3.19; O, 30.17.

EXAMPLE 27

7-(3,5-dimethoxy-4-hydroxycinnamoyl)amino-3-octyloxy-4-(tetra-O-acetyl-β-D-galactopyranosyloxy)-1-methyl-2(1H)-quinolinone (compound 25)

In accordance with EXAMPLE 13, 7-amino-3-octyloxy-4-(tetra-O-acetyl-β-D-galactopyranosyloxy)-1-methyl-2(1H)-quinolinone and 3,5-dimethoxy-4-hydroxycinnamic acid were used instead of 7-amino-3-octyloxy-4-(6-O-methyl-2,3,4-triacetyl-β-D-glcuropyranosyloxy)-1-methyl-2(1H)-quinolinone and 3,5-dimethoxy-4-(6-O-methyl-2,3,4-triacetyl-α-D-glcuropyranosyloxy)cinnamic acid, the title compound (25) was obtained.

$^1$H-NMR (CDCl$_3$, δ-TMS) 8.30(s, 1H), 8.01(d, 1H, J=8.0 Hz), 7.83(d, 1H, J=8.4 Hz), 7.64(d, 1H, J=15.2 Hz), 7.05(m, 1H), 6.73(s, 2H), 6.51(d, 1H, J=15.2 Hz), 5.90(d, 1H, J=7.6 Hz), 5.35(m, 5H), 4.15(m, 4H), 3.84(s, 6H), 3.71(s, 3H), 3.67(s, 3H), 2.04(m, 9H), 1.40~1.20(m, 12H), 0.88(m, 3H)

IR (KBr, cm$^{-1}$): 3350, 1745, 1680, 1250
Elemental analysis for: $C_{43}H_{54}N_2O_{16}$
Calculated (%): C, 60.41; H, 6.37; N, 3.28; O, 29.94.
Found (%): C, 60.45; H, 6.23; N, 3.19; O, 30.13.

EXAMPLE 28

7-[3,5-dimethoxy-4-(β-D-galactopyranosyloxy) cinnamoyl]amino-3-octyloxy-4-(β-D-galactopyranosyloxy)-1-methyl-2(1H)-quinolinone (compound 26)

In accordance with EXAMPLE 16, 7-[3,5-dimethoxy-4-(tetra-O-acetyl-β-D-galactopyranosyloxy)cinnamoyl]amino-3-octyloxy-4-(tetra-O-acetyl-β-D-galactopyranosyloxy)-1-methyl-2(1H)-quinolinone was used instead of 7-[(3,5-dimethoxy-4-(6-O-methyl-2,3,4-triacetyl-β-D-glcuropyranosyloxy)cinnamoyl]amino-3-octyloxy-4-(6-O-methyl-2,3,4-triacetyl-β-D-glcuropyranosyloxy)-1-methyl-2(1H)-quinolinone, the title compound (26) was obtained.

$^1$H-NMR (d$_6$-DMSO, δ-TMS) 11.05(s, 1H), 8.12(s, 1H), 7.86(d, 1H, J=8.8 Hz), 7.46(m, 3H), 7.02(m, 3H), 6.80(s, 1H), 6.60(s, 1H), 5.52~4.99(m, 6H), 4.11(m, 5H), 4.01(m, 1H), 3.84(s, 6H), 3.55(s, 3H), 3.27~3.17(m, 9H), 1.65~1.15 (m, 12H), 0.86(m, 3H)

IR (KBr, cm$^{-1}$): 3350, 1680, 1250
Elemental analysis for: $C_{41}H_{56}N_2O_{17}$
Calculated (%): C, 58.01; H, 6.65; N, 3.30; O, 32.04.
Found (%): C, 57.99; H, 6.78; N, 3.31; O, 31.92.

EXAMPLE 29

7-[3,5-dimethoxy-4-(β-D-galactopyranosyloxy) cinnamoyl]amino-3-octyloxy-4-hydroxy-1-methyl-2 (1H)-quinolinone (compound 27)

In accordance with EXAMPLE 16, 7-[3,5-dimethoxy-4-(tetra-O-acetyl-β-D-galactopyranosyloxy)cinnamoyl]amino-3-octyloxy-4-hydroxy-1-methyl-2(1H)-quinolinone was used instead of 7-[(3,5-dimethoxy-4-(6-O-methyl-2,3,4-triacetyl-β-D-glcuropyranosyloxy)cinnamoyl]amino-3-octyloxy-4-(6-O-methyl-2,3,4-triacetyl-β-D-glcuropyranosyloxy)-1-methyl-2(1H)-quinolinone, the title compound (27) was obtained.

$^1$H-NMR (d$_6$-DMSO, δ-TMS) 10.75(s, 1H), 8.02(s, 1H), 7.84(d, 1H, J=8.8 Hz),7.55(m, 3H), 6.99(m, 3H), 6.87(d, 1H, J=15.6 Hz), 5.09(s, 2H), 5.07(m, 1H), 4.10(m, 2H), 3.96(t, 2H, J=7.2 Hz), 3.84(s, 6H), 3.56(s, 3H), 3.42~3.18(m, 5H), 1.72~1.15(m, 12H), 0.86(m, 3H) IR (KBr, cm$^{-1}$): 3350, 1680, 1220

Elemental analysis for: $C_{35}H_{46}N_2O_{12}$
Calculated (%): C, 61.21; H, 6.75; N, 4.08; O, 27.96.
Found (%): C, 61.09; H, 6.85; N, 4.02; O, 28.04.

EXAMPLE 30

7-(3,5-dimethoxy-4-hydroxycinnamoyl)amino-3-octyloxy-4-(β-D-galactopyranosyloxy)-1-methyl-2 (1H)-quinolinone (compound 28)

In accordance with EXAMPLE 16, 7-(3,5-dimethoxy-4-hydroxy cinnamoyl)amino-3-octyloxy-4-(tetra-O-acetyl-β-D-galactopyranosyloxy)-1-methyl-2(1H)-quinolinone was used instead of 7-[(3,5-dimethoxy-4-(6-O-methyl-2,3,4-triacetyl-β-D-glcuropyranosyloxy)cinnamoyl]amino-3-octyloxy-4-(6-O-methyl-2,3,4-triacetyl-β-D-glcuropyranosyloxy)-1-methyl-2(1H)-quinolinone, the title compound (28) was obtained.

$^1$H-NMR (d$_6$-DMSO, δ-TMS) 10.30(s, 1H), 8.08(s, 1H), 7.90(d, 1H, J=8.8 Hz), 7.44(m, 2H), 7.30(s, 1H), 6.79(s, 2H), 6.45(d, 1H, J=15.6 Hz), 5.48(d, 1H, J=7.6 Hz), 5.32(s, 1H), 4.97(s, 1H), 4.16(m, 3H), 3.99(m, 1H), 3.75(s, 6H), 3.58(s, 3H), 3.30~3.10(m, 6H), 1.72~1.20(m, 12H), 0.87(m, 3H)

IR (KBr, cm$^{-1}$): 3350, 1680, 1220
Elemental analysis for: $C_{35}H_{46}N_2O_{12}$
Calculated (%): C, 61.21; H, 6.75; N, 4.08; O, 27.96.
Found (%): C, 61.24; H, 6.77; N, 4.06; O, 27.93.

EXAMPLE 31

7-[3,5-dimethoxy-4-(tetra-O-acetyl-α-D-mannopyranosyloxy)cinnamoyl]amino-3-octyloxy-4-(tetra-O-acetyl-α-D-mannopyranosyloxy)-1-methyl-2(1H)-quinolinone (compound 29)

In accordance with EXAMPLE 13, 7-amino-3-octyloxy-4-(tetra-O-acetyl-α-D-mannopyranosyloxy)-1-methyl-2 (1H)-quinolinone and 3,5-dimethoxy-4-(tetra-O-acetyl-α-D-mannopyranosyloxy)cinnamic acid were used instead of 7-amino-3-octyloxy-4-(6-O-methyl-2,3,4-triacetyl-β-D-glcuropyranosyloxy)-1-methyl-2(1H)-quinolinone and 3,5-dimethoxy-4-(6-O-methyl-2,3,4-triacetyl-β-D-glcuropyranosyloxy)cinnamic acid, the title compound (29) was obtained.

$^1$H-NMR (CDCl$_3$, δ-TMS) 8.28(s, 1H), 8.01(d, 1H, J=8.0 Hz), 7.83(d, 1H, J=8.4 Hz), 7.64(d, 1H, J=15.2 Hz) 7.08(m, 1H), 6.73(s, 2H), 6.51(d, 1H, J=15.2 Hz), 5.78(d, 1H, J=7.6 Hz), 5.49(m, 1H), 5.32(m, 7H), 4.10(m, 7H), 3.84(s, 6H), 3.71(s, 6H), 3.67(s, 3H), 2.04(m, 18H), 1.40~1.20(m, 12H), 0.87(m, 3H)

IR (KBr, cm$^{-1}$): 3350, 1745, 1680
Elemental analysis for: $C_{57}H_{72}N_2O_{25}$
Calculated (%): C, 57.77; H, 6.12; N, 2.36; O, 33.75.
Found (%): C, 57.70; H, 6.09; N, 2.45; O, 33.76.

EXAMPLE 32

7-[3,5-dimethoxy-4-(tetra-O-acetyl-α-D-mannopyranosyloxy)cinnamoyl]amino-3-octyloxy-4-hydroxy-1-methyl-2(1H)-quinolinone (compound 30)

In accordance with EXAMPLE 13, 7-amino-3-octyloxy-4-hydroxyl-methyl-2(1H)-quinolinone and 3,5-dimethoxy-4-(tetra-O-acetyl-α-D-mannopyranosyloxy)cinnamic acid were used instead of 7-amino-3-octyloxy-4-(6-O-methyl-2,3,4-triacetyl-β-D-glcuropyranosyloxy)-1-methyl-2(1H)-quinolinone and 3,5-dimethoxy-4-(6-O-methyl-2,3,4-triacetyl-β-D-glcuropyranosyloxy)cinnamic acid, the title compound (30) was obtained.

$^1$H-NMR (CDCl$_3$, δ-TMS) 8.37(s, 1H), 8.05(d, 1H, J=8.0 Hz), 7.83(d, 1H, J=8.4 Hz), 7.64(d, 1H, J=15.2 Hz), 7.08(m, 1H), 6.72(s, 2H), 6.51(d, 1H, J=15.2 Hz), 5.52(m, 1H), 5.35(m, 5H), 4.15(m, 4H), 3.84(s, 6H), 3.71(s, 3H), 3.67(s, 3H), 2.04(m, 9H), 1.40~1.20(m, 12H), 0.88(m, 3H)

IR (KBr, cm$^{-1}$): 3350, 1745, 1680, 1220
Elemental analysis for: $C_{42}H_{54}N_2O_{16}$
Calculated (%): C, 60.41; H, 6.37; N, 3.28; O, 29.94.
Found (%): C, 60.45; H, 6.28; N, 3.30; O, 29.97.

EXAMPLE 33

7-(3,5-dimethoxy-4-hydroxycinnamoyl)amino-3-octyloxy-4-(tetra-O-acetyl-α-D-mannopyranosyloxy)-1-methyl-2(1H)-quinolinone (compound 31)

In accordance with EXAMPLE 13, 7-amino-3-octyloxy-4-(tetra-O-acetyl-α-D-mannopyranosyloxy)-1-methyl-2

(1H)-quinolinone and 3,5-dimethoxy-4-hydroxycinnamic acid were used instead of 7-amino-3-octyloxy-4-(6-O-methyl-2,3,4-triacetyl-β-D-glcuropyranosyloxy)-1-methyl-2(1H)-quinolinone and 3,5-dimethoxy-4-(6-)-methyl-2,3,4-triacetyl-β-D-glcuropyranosyloxy)cinnamic acid, the title compound (31) was obtained.

$^1$H-NMR (CDCl$_3$, δ-TMS) 8.30(s, 1H), 8.01(d, 1H, J=8.0 Hz), 7.83(d, 1H, J=8.4 Hz), 7.64(d, 1H, J=15.2 Hz), 7.05(m, 1H), 6.73(s, 2H), 6.51(d, 1H, J=15.2 Hz), 5.90(d, 1H, J=7.6 Hz), 5.35(m, 5H), 4.15(m, 4H), 3.84(s, 6H), 3.71(s, 3H), 3.67(s, 3H), 2.04(m, 9H), 1.40~1.20(m, 12H), 0.88(m, 3H)

IR (KBr, cm$^{-1}$): 3350, 1745, 1680, 1250

Elemental analysis for: C$_{42}$H$_{54}$N$_2$O$_{16}$

Calculated (%): C, 60.41; H, 6.37; N, 3.28; O, 29.94.

Found (%): C, 60.38; H, 6.33; N, 3.37; O, 29.92.

EXAMPLE 34

7-[3,5-dimethoxy-4-(α-D-mannopyranosyloxy)cinnamoyl]amino-3-octyloxy-4-(α-D-mannopyranosyloxy)-1-methyl-2(1H)-quinolinone (compound 32)

In accordance with EXAMPLE 16, 7-[3,5-dimethoxy-4-(tetra-O-acetyl-α-D-mannopyranosyloxy)cinnamoyl]amino-3-octyloxy-4-(tetra-O-acetyl-α-D-mannopyranosyloxy)-1-methyl-2(1H)-quinolinone was used instead of 7-[3,5-dimethoxy-4-(6-O-methyl-2,3,4-triacetyl-β-D-glcuropyranosyloxy)cinnamoyl]amino-3-octyloxy-4-(6-O-methyl-2,3,4-triacetyl-β-D-glcuropyranosyloxy)-1-methyl-2(1H)-quinolinone, the title compound (32) was obtained.

$^1$H-NMR (d$_6$-DMSO, δ-TMS) 11.05(s, 1H), 8.12(s, 1H), 7.86(d, 1H, J=8.8 Hz), 7.38(m, 3H), 7.02(m, 3H), 6.80(s, 1H), 6.58(s, 1H), 5.52~4.99(m, 6H), 4.11(m, 5H), 4.01(m, 1H), 3.84(s, 6H), 3.55(s, 3H), 3.27~3.17(m, 9H), 1.65~1.15(m, 12H), 0.86(m, 3H)

IR (KBr, cm$^{-1}$): 3350, 1680, 1220

Elemental analysis for: C$_{41}$H$_{56}$N$_2$O$_{17}$

Calculated (%): C, 58.01; H, 6.65; N, 3.30; O, 32.04.

Found (%): C, 58.10; H, 6.54; N, 3.29; O, 32.07.

EXAMPLE 35

7-[3,5-dimethoxy-4-(α-D-mannopyranosyloxy)cinnamoyl]amino-3-octyloxy-4-hydroxy-1-methyl-2(1H)-quinolinone (compound 33)

In accordance with EXAMPLE 16, 7-[3,5-dimethoxy-4-(tetra-O-acetyl-α-D-mannopyranosyloxy)cinnamoyl]amino-3-octyloxy-4-hydroxy-1-methyl-2(1H)-quinolinone was used instead of 7-[3,5-dimethoxy-4-(6-O-methyl-2,3,4-triacetyl-β-D-glcuropyranosyloxy)cinnamoyl]amino-3-octyloxy-4-(6-O-methyl-2,3,4-triacetyl-β-D-glcuropyranosyloxy)-1-methyl-2(1H)-quinolinone, the title compound (33) was obtained.

$^1$H-NMR (d$_6$-DMSO, δ-TMS) 10.75(s, 1H), 8.02(s, 1H), 7.84(d, 1H, J=8.8 Hz), 7.55(m, 3H), 6.99(m, 3H), 6.87(d, 1H, J=15.6 Hz), 5.09(s, 2H), 5.07(m, 1H), 4.10(m, 2H), 3.98(t, 2H, j=7.2 Hz), 3.84(s, 6H), 3.56(s, 3H), 3.42~3.18(m, 5H), 1.72~1.15(m, 12H), 0.86(m, 3H)

IR (KBr, cm$^{-1}$): 3350, 1680, 1220

Elemental analysis for: C$_{35}$H$_{46}$N$_2$O$_{12}$

Calculated (%): C, 61.21; H, 6.75; N, 4.08; O, 27.96.

Found (%): C, 61.09; H, 6.85; N, 4.02; O, 28.04.

EXAMPLE 36

7-(3,5-dimethoxy-4-hydroxy cinnamoyl)amino-3-octyloxy-4-(α-D-mannopyranosyloxy)-1-methyl-2(1H)-quinolinone (compound 34)

In accordance with EXAMPLE 16, 7-(3,5-dimethoxy-4-hydroxy cinnamoyl)amino-3-octyloxy-4-(tetra-O-acetyl-α-D-mannopyranosyloxy)-1-methyl-2(1H)-quinolinone was used instead of 7-[3,5-dimethoxy-4-(6-O-methyl-2,3,4-triacetyl-β-D-glcuropyranosyloxy)cinnamoyl]amino-3-octyloxy-4-(6-O-methyl-2,3,4-triacetyl-β-D-glcuropyranosyloxy)-1-methyl-2(1H)-quinolinone, the title compound (34) was obtained.

$^1$H-NMR (d$_6$-DMSO, δ-TMS) 10.30(s, 1H), 8.08(s, 1H), 7.90(d, 1H, J=8.8 Hz), 7.38(m, 2H), 7.28(s, 1H), 6.80(s, 2H), 6.45(d, 1H, J=15.6 Hz), 5.48(d, 1H, J=7.6 Hz), 5.32(s, 1H), 4.97(s, 1H), 4.16(m, 3H), 3.99(m, 1H), 3.75(s, 6H), 3.58(s, 3H), 3.30~3.10(m, 6H), 1.72~1.20(m, 12H), 0.87(m, 3H)

IR (KBr, cm$^{-1}$): 3350, 1680, 1220

Elemental analysis for: C$_{35}$H$_{46}$N$_2$O$_{12}$

Calculated (%): C, 61.21; H, 6.75; N, 4.08; O, 27.96.

Found (%): C, 61.09; H, 6.78; N, 4.18; O, 27.95.

EXAMPLE 37

7-[3,5-dimethoxy-4-(6-O-methyl-2,3,4-tribenzoyl-β-D-glcuropyranosyloxy)cinnamoyl]amino-3-octyloxy-4-(6-O-methyl-2,3,4-tribenzoyl-β-D-glcuropyranosyloxy)-1-methyl-2(1H)-quinolilnone (compound 35)

In accordance with EXAMPLE 13, 3,5-dimethoxy-4-(6-O-methyl-2,3,4-tribenzoyl-β-D-glucuropyranosyloxy)cinnamic acid and 7-amino-3-octyloxy-4-(6-O-methyl-2,3,4-tribenzoyl-β-D-glucuropyranosyloxy)-1-methyl-2(1H)-quinolinone were used instead of 3,5-dimethoxy-4-(6-O-methyl-2,3,4-triacetyl-β-D-glcuropyranosyloxy)cinnamic acid and 7-amino-3-octyloxy-4-(6-O-methyl-2,3,4-triacetyl-β-D-glcuropyranosyloxy)-1-methyl-2(1H)-quinolinone, the title compound (35) was obtained.

$^1$H-NMR (CDCl$_3$, δ-TMS) 8.24(s, 1H), 8.01(d, 1H, J=8.0 Hz), 7.83~7.23(m, 32H), 7.08(m, 1H), 6.73(s, 2H), 6.51(d, 1H, J=15.2 Hz), 5.89(d, 1H, J=7.6 Hz), 5.45(m, 1H), 5.32(m, 7H), 4.09(m, 3H), 3.84(s, 6H), 3.71(s, 6H), 3.67(s, 3H), 1.40~1.20(m, 12H), 0.88(m, 3H)

IR (KBr, cm$^{-1}$): 3350, 1745, 1680, 1220

Elemental analysis for: C$_{85}$H$_{80}$N$_2$O$_{25}$

Calculated (%): C, 66.75; H, 5.27; N, 1.83; O, 26.15.

Found (%): C, 66.83; H, 5.19; N, 1.89; O, 26.09.

EXAMPLE 38

7-[3,5-dimethoxy-4-(6-O-methyl-2,3,4-tribenzyl-β-D-glcuropyranosyloxy)cinnamoyl]amino-3-octyloxy-4-(6-O-methyl-2,3,4-tribenzyl-β-D-glcuropyranosyloxy)-1-methyl2(1H)-quinolinone (compound 36)

In accordance with EXAMPLE 13, 3,5-dimethoxy-4-(6-O-methyl-2,3,4-tribenzyl-β-D-glucuropyranosyloxy)cinnamic acid and 7-amino-3-octyloxy-4-(6-O-methyl-2,3,4-tribenzyl-β-D-glucuropyranosyloxy)-1-methyl-2(1H)-quinolinone were used instead of 3,5-dimethoxy-4-(6-O-methyl-2,3,4-triacetyl-β-D-glcuropyranosyloxy)cinnamic acid and 7-amino-3-octyloxy-4-(6-O-methyl-2,3,4-triacetyl-β-D-glcuropyranosyloxy)-1-methyl-2(1H)-quinolinone, the title compound (36) was obtained.

$^1$H-NMR (CDCl$_3$, δ-TMS) 8.31(s, 1H), 8.01(d, 1H, J=8.0 Hz), 7.77~7.23(m, 32H), 7.08(m, 1H), 6.73(s, 2H), 6.51(d, 1H, J=15.2 Hz), 5.89(d, 1H, J=7.6 Hz), 5.45(m, 1H), 5.32(m, 7H), 5.05(m, 12H), 4.09(m, 3H), 3.84(s, 6H), 3.71(s, 6H), 3.67(s, 3H), 1.40~1.20(m, 12H), 0.88(m, 3H)

IR (KBr, cm$^{-1}$): 3350, 1715, 1680, 1220
Elemental analysis for: $C_{85}H_{92}N_2O_{19}$
Calculated (%): C, 70.62; H, 6.41; N, 1.94; O, 21.03.
Found (%): C, 70.56; H, 6.39; N, 1.99; O, 21.06.

EXAMPLE 39

7-amino-3-octyloxy-4-(6-O-methyl-2,3,4-tribenzyl-β-D-glcuropyranosyloxy)-1-methyl-2(1H)-quinolinone (compound 2)

To a mixture of 400 mg of 7-nitro-3-octyloxy-4-(6-O-methyl-2,3,4-tribenzyl-β-D-glcuropyranosyloxy)-1-methyl-2(1H)-quinolinone (0.60 mmol) in 8 ml of ethanol and 16 ml of toluene was added 200 mg of zinc powder at 20° C. After the mixture was stirred at 50° C., 1 ml of acetic acid was added. Further, the mixture was stirred at 50° C. for 3 hours. The reaction mixture was filtered and the filtrate was concentrated under reduced pressure. The resulting crude product was crystallized from diethyl ether to give 313 mg of title compound (2). (yield=82%)

EXAMPLE 40

7-[3,5-dimethoxy-4-(6-O-methyl-2,3,4-triacetyl-β-D-glcuropyranosyloxy)cinnamoyl]amino-3-octyloxy-4-(6-O-methyl-2,3,4-triacetyl-β-D-glcuropyranosyloxy)-1-methyl-2(1H)-quinolinone (compound 11)

To a mixture of 70.0 mg of sodium hydride (purity 60%, 1.75 mmol) in 3 ml of N,N-dimethylformamide was added a 300 mg of 7-(3,5-dimethoxy-4-hydroxycinnamoyl)amino-3-octyloxy-4-hydroxy-1-methyl-2(1H)-quinolinone (0.57 mmol) at room temperature. After the mixture was stirred at 0 to 10° C. for 30 minutes, 454 mg of Methyl 1-bromo-2,3,4-triacetylglucuronate (1.15 mmol) was added. After the mixture was stirred at room temperature for 3 hours, 2 mol/l of aqueous hydrogen chloride solution was added, and extracted with ethyl acetate. The organic layer was washed with water, and concentrated under reduced pressure to give a crude product. Purification of this crude product by column chromatography gave 334 mg of title compound (11). (yield=52%)

EXAMPLE 41

Ethyl 3,5-dimethoxy-4-(6-O-methyl-2,3,4-triacetyl-β-D-glcuropyranosyloxy)cinnamate (compound 37)

To a mixture of 70.0 mg of sodium hydride (purity 60%, 1.75 mmol) in 3 ml of N, N-dimethylformamide was added a 300 mg of Ethyl 3,5-dimethoxy-4-hydroxycinnamate (1.19 mmol) at room temperature. After the mixture was stirred at 0 to 10° C. for 30 minutes, 473 mg of Methyl 1-bromo-2,3,4-triacetylglucuronate (1.20 mmol) was added. After the mixture was stirred at room temperature for 3 hours, 2 mol/l of aqueous hydrogen chloride solution was added, and extracted with ethyl acetate. The organic layer was washed with water, and concentrated under reduced pressure to give a crude product. Purification of this crude product by column chromatography gave 460 mg of title compound (11). (yield=68%)

$^1$H-NMR (CDCl$_3$, δ-TMS) 7.08(m, 1H), 6.73(s, 3H), 6.51(d, 1H, J=15.2 Hz), 5.84(d, 1H, J=7.2 Hz), 5.41~5.28(m, 3H), 4.21(t, 2H, J=7.2 Hz), 4.08(d, 1H, J=9.2 Hz), 3.78(s, 6H), 2.07(s, 3H), 2.04(s, 3H), 2.02(s, 3H), 1.25(t, 3H, J=6.8 Hz)

IR (KBr, cm$^{-1}$): 2850, 1740, 1250
Elemental analysis for: $C_{26}H_{32}O_{14}$
Calculated (%): C, 54.93; H, 5.67; O, 39.40.
Found (%): C, 54.95; H, 5.69; O, 39.36.

EXAMPLE 42

3,5-dimethoxy-4-(β-D-glcuropyranosyloxy)cinnamic acid (compound 38)

In accordance with EXAMPLE 9, Ethyl 3,5-dimethoxy-4-(6-O-methyl-2,3,4-triacetyl-β-D-glcuropyranosyloxy)cinnamate was used instead of 7-amino-3-octyloxy-4-(6-O-methyl-2,3,4-triacetyl-β-D-glcuropyranosyloxy)-1-methyl-2(1H)-quinolinone, the title compound (38) was obtained.

$^1$H-NMR (d$_6$-DMSO, δ-TMS) 7.10(m, 1H), 6.73(s, 2H), 6.51(d, 1H, J=15.2 Hz), 5.84(d, 1H, J=7.2 Hz), 5.41~5.28(m, 3H), 4.08(d, 1H, J=9.2 Hz), 3.78(s, 6H)

IR (KBr, cm$^{-1}$): 3340, 2850, 1740
Elemental analysis for: $C_{17}H_{20}O_{11}$
Calculated (%): C, 51.00; H, 5.04; O, 43.96.
Found (%): C, 50.95; H, 5.09; O, 43.96.

EXAMPLE 43

7-amino-3-octyloxy-4-(tetra-O-acetyl-β-D-glucopyranosyloxy)-1-methyl-2(1H)-quinolinone (compound 3)

In accordance with EXAMPLE 39, Ethyl 7-nitro-3-octyloxy-4-(tetra-O-acetyl-β-D-glucopyranosyloxy)-1-methyl-2(1H)-quinolinone was used instead of 7-nitro-3-octyloxy-4-(6-O-methyl-2,3,4-triacetyl-β-D-glcuropyranosyloxy)-1-methyl-2(1H)-quinolinone, the title compound (3) was obtained.

EXAMPLE 44

7-amino-3-octyloxy-4-(tetra-O-acetyl-β-D-galactopyranosyloxy)-1-methyl-2(1H)-quinolinone (compound 4)

In accordance with EXAMPLE 39, Ethyl 7-nitro-3-octyloxy-4-(tetra-O-acetyl-β-D-galactopyranosyloxy)-1-methyl-2(1H)-quinolinone was used instead of 7-nitro-3-octyloxy-4-(6-O-methyl-2,3,4-triacetyl-β-D-glcuropyranosyloxy)-1-methyl-2(1H)-quinolinone, the title compound (4) was obtained.

EXAMPLE 45

7-amino-3-octyloxy-4-(tetra-O-acetyl-α-D-mannopyranosyloxy)-1-methyl-2(1H)-quinolinone (compound 5)

In accordance with EXAMPLE 39, Ethyl 7-nitro-3-octyloxy-4-(tetra-O-acetyl-α-D-mannopyranosyloxy)-1-methyl-2(1H)-quinolinone was used instead of 7-nitro-3-octyloxy-4-(6-O-methyl-2,3,4-triacetyl-β-D-glcuropyranosyloxy)-1-methyl-2(1H)-quinolinone, the title compound (5) was obtained.

EXAMPLE 46

7-[3,5-dimethoxy-4-(6-O-methyl-2,3,4-tribenzoyl-β-D-glcuropyranosyloxy)cinnamoyl]amino-3-ocyloxy-4-(6-O-methyl-2,3,4-tribenzoyl-β-D-glcuropyranosyloxy)-1-methyl-2(1H)-quinolinone (compound 35)

In accordance with EXAMPLE 46, Methyl 1-bromo-2,3,4-tribenzylglucuronate was used instead of Methyl 1-bromo-2,3,4-triacetylglucuronate, the title compound (35) was obtained.

EXAMPLE 47

7-[3,5-dimethoxy-4-(6-O-methyl-2,3,4-tribenzyl-β-D-glcuropyranosyloxy)cinnamoyl]amino-3-octyloxy-4-(6-O-methyl-2,3,4-tribenzyl-β-D-glcuropyranosyloxy)-1-methyl-2(1H)-quinolinone (compound 36)

In accordance with EXAMPLE 40, Methyl 1-bromo-2,3,4-tribenzylglucuronate was used instead of Methyl 1-bromo-2,3,4-triacetylglucuronate, the title compound (36) was obtained.

EXAMPLE 48

7-[3,5-dimethoxy-4-(tetra-O-acetyl-β-D-glucopyranosyloxy)cinnamoyl]amino-3-octyloxy-4-(tetra-O-acetyl-β-D-glucopyranosyloxy)-1-methyl-2(H)-quinolinone (compound 17)

In accordance with EXAMPLE 40, tetra-O-acetyl-β-D-glucopyranosyl bromide was used instead of Methyl 1-bromo-2,3,4-triacetylglucuronate, the title compound (17) was obtained.

EXAMPLE 49

7-[3,5-dimethoxy-4-(tetra-O-acetyl-β-D-galactopyranosyloxy)cinnamoyl]amino-3-octyloxy-4-(β-D-galactopyranosyloxy)-1-methyl-2(1H)-quinolinone (compound 23)

In accordance with EXAMPLE 40, tetra-O-acetyl-β-D-galactopyranosyloxy bromide was used instead of Methyl 1-bromo-2,3,4-triacetylglucuronate, the title compound (23) was obtained.

EXAMPLE 50

7-[3,5-dimethoxy-4-(tetra-O-acetyl-α-D-mannopyranosyloxy)cinnamoyl]amino-3-octyloxy-4-(tetra-O-acetyl-α-D-mannopyranosyloxy)-1-methyl-2(1H)-quinolinone (compound 29)

In accordance with EXAMPLE 40, tetra-O-acetyl-α-D-mannopyranosyloxy bromide was used instead of Methyl 1-bromo-2,3,4-triacetylglucuronate, the title compound (29) was obtained.

EXAMPLE 51

1,1,1-Trichloroethyl 3,5-dimethoxy-4-(6-O-methyl-2,3,4-triacetyl-β-D-glcuropyranosyloxy)cinnamate (compound 39)

In accordance with EXAMPLE 41, 1,1,1-Trichloroethyl 3,5-dimethoxy-4-hydroxycinnamate was used instead of Ethyl 3,5-dimethoxy-4-hydroxycinnamate, the title compound (39) was obtained.

$^1$H-NMR (CDCl$_3$, δ-TMS) 7.08(m, 1H), 6.73(s, 3H), 6.51(d, 1H, J=15.2 Hz), 5.84(d, 1H, J=7.2 Hz), 5.41~5.28(m, 3H), 4.78(s, 2H), 4.21(t, 2H, J=7.2 Hz), 4.08(d, 1H, J=9.2 Hz), 3.78(s, 6H), 2.07(s, 3H), 2.04(s, 3H), 2.02(s, 3H)

IR (KBr, cm$^{-1}$): 2850, 1740, 1250

Elemental analysis for: C$_{26}$H$_{32}$O$_{14}$Cl$_3$

Calculated (%): C, 46.48; H, 4.35; O, 33.34; Cl, 15.83.

Found (%): C, 46.54; H, 4.29; O, 33.42; Cl, 15.75.

EXAMPLE 52

3,5-dimethoxy-4-(6-O-methyl-2,3,4-triacetyl-β-D-glcuropyranosyloxy)cinnamic acid (compound 40)

To a solution of 15.0 g of 1,1,1-Trichloroethyl 3,5-dimethoxy-4-(6-O-methyl-2,3,4-triacetyl-β-D-glcuropyranosyloxy cinnamate (22.3 mmol) in 300 ml of acetic acid was added 36 g of zinc powder at room temperature. After the mixture was stirred at room temperature for 3 hours. The reaction mixture was filtered and the filtrate was concentrated under reduced pressure. The resulting crude product was crystallized from ethyl acetate and hexane to give 11.3 g of title compound (40). (yield=93%)

$^1$H-NMR (d$_6$-DMSO, δ-TMS) 12.25(bs, 1H), 7.51(d, 1H, J=15.6 Hz), 7.05(s, 2H), 6.56(d, 1H, J=16.0 Hz), 5.45~5.30 (m, 2H), 4.46(d, 1H, J=9.6 Hz), 3.78(s, 6H), 3.61(s, 6H), 1.99(s, 3H), 1.98(s, 3H), 1.97(s, 3H)

IR (KBr, cm$^{-1}$): 3340, 2850, 1740

Elemental analysis for: C$_{24}$H$_{28}$O$_{14}$

Calculated (%): C, 53.33; H, 5.22; O, 41.45.

Found (%): C, 53.30; H, 5.19; O, 41.41.

EXAMPLE 53

1,1,1-Trichloroethyl 3,5-dimethoxy-4-(tetra-O-acetyl-β-D-glucopyranosyloxy) cinnamate (compound 41)

In accordance with EXAMPLE 41, 1,1,1-Trichloroethyl 3,5-dimethoxy-4-hydroxycinnamate and tetra-O-acetyl-β-D-glucopyranosyl bromide were used instead of Ethyl 3,5-dimethoxy-4-hydroxycinnamate and Methyl 1-bromo-2,3,4-triacetylglucuronate, the title compound (41) was obtained.

$^1$H-NMR (CDCl$_3$, δ-TMS) 7.50(d, 1H, J=15.6 Hz), 7.05 (s, 2H), 6.55(d, 1H, J=16.0 Hz), 5.74(d, 1H, J=9.6 Hz) 5.50~5.10(m, 3H), 4.78(s, 2H), 4.45~4.00(m, 3H), 3.78(s, 6H), 2.10(s, 3H), 2.07(s, 3H), 2.04(s, 3H), 2.02(s, 3H)

IR (KBr, cm$^{-1}$): 2850, 1740, 1250

Elemental analysis for: C$_{27}$H$_{31}$O$_{14}$Cl$_3$

Calculated (%): C, 47.28; H, 4.56; O, 32.66; Cl, 15.50.

Found (%): C, 47.36; H, 4.49; O, 32.61; Cl, 15.54.

EXAMPLE 54

3,5-dimethoxy-4-(tetra-O-acetyl-β-D-glucopyranosyloxy) cinnamic acid (compound 42)

In accordance with EXAMPLE 52, 1,1,1-Trichloroethyl 3,5-dimethoxy-4-(tetra-O-acetyl-β-D-glucopyranosyloxy) cinnamate was used instead of 1,1,1-Trichloroethyl 3,5-dimethoxy-4-(6-O-methyl-2,3,4-triacetyl-β-D-glcuropyranosyloxy)cinnamate, the title compound (42) was obtained.

$^1$H-NMR (d$_6$-DMSO, δ-TMS) 12.25(bs, 1H), 7.50(d, 1H, J=15.6 Hz), 7.05(s, 2H), 6.56(d, 1H, J=16.0 Hz), 5.71(d, 1H, J=9.6 Hz), 5.50~5.10(m, 3H), 4.45~4.00(m, 3H), 3.79(s, 6H), 2.10(s, 3H), 2.07(s, 3H), 2.04(s, 3H), 2.02(s, 3H)

IR (KBr, cm$^{-1}$): 3340, 2850, 1740

Elemental analysis for: C$_{25}$H$_{30}$O$_{14}$

Calculated (%): C, 54.15; H, 5.46; O, 40.39.

Found (%): C, 54.24; H, 5.42; O, 40.34.

EXAMPLE 55

1,1,1-Trichloroethyl 3,5-dimethoxy-4-(tetra-O-acetyl-β-D-galactopyranosyloxy) cinnamate (compound 43)

In accordance with EXAMPLE 41, 1,1,1-Trichloroethyl 3,5-dimethoxy-4-hydroxycinnamate and tetra-O-acetyl-β-D-galactopyranosyl bromide were used instead of Ethyl 3,5-dimethoxy-4-hydroxycinnamate and Methyl 1-bromo-2,3,4-triacetylglucuronate, the title compound (43) was obtained.

$^1$H-NMR (CDCl$_3$, δ-TMS) 7.54(d, 1H, J=15.6 Hz), 7.05 (s, 2H), 6.54(d, 1H, J=16.0 Hz), 5.70(d, 1H, J=9.6 Hz) 5.50~5.10(m, 3H), 4.78(s, 2H), 4.45~4.00(m, 3H), 3.78(s, 6H), 2.13(s, 3H), 2.10(s, 3H), 2.09(s, 3H), 2.05(s, 3H)

IR (KBr, cm$^{-1}$): 2850, 1740, 1250

Elemental analysis for: C$_{27}$H$_{31}$O$_{14}$Cl$_3$

Calculated (%): C, 47.28; H, 4.56; O, 32.66; Cl, 15.50.

Found (%): C, 47.23; H, 4.51; O, 32.72; Cl, 15.54.

EXAMPLE 56

3,5-dimethoxy-4-(tetra-O-acetyl-β-D-galactopyranosyloxy)cinnamic acid (compound 44)

In accordance with EXAMPLE 52, 1,1,1-Trichloroethyl 3,5-dimethoxy-4-(tetra-O-acetyl-β-D-glucopyranosyloxy) cinnamate was used instead of 1,1,1-Trichloroethyl 3,5-dimethoxy-4-(6-O-methyl-2,3,4-triacetyl-β-D-glcuropyranosyloxy cinnamate, the title compound (44) was obtained.

$^1$H-NMR (CDCl$_3$, δ-TMS) 12.21(bs, 1H), 7.53(d, 1H, J=15.6 Hz), 7.05(s, 2H), 6.52(d, 1H, J=16.0 Hz), 5.65(d, 1H, J=9.6 Hz), 5.50~5.10(m, 3H), 4.45~4.00(m, 3H), 3.78(s, 6H), 2.13(s, 3H), 2.10(s, 3H), 2.09(s, 3H), 2.05(s, 3H)

IR (KBr, cm$^{-1}$): 3340, 2850, 1740

Elemental analysis for: C$_{25}$H$_{30}$O$_{14}$

Calculated (%): C, 54.15; H, 5.46; O, 40.39.

Found (%): C, 54.16; H, 5.38; O, 40.46.

EXAMPLE 57

1,1,1-Trichloroethyl 3,5-dimethoxy-4-(tetra-O-acetyl-α-D-mannopyranosyloxy)cinnamate (compound 45)

In accordance with EXAMPLE 41, 1,1,1-Trichloroethyl 3,5-dimethoxy-4-hydroxycinnamate and tetra-O-acetyl-α-D-mannopyranosyl bromide were used instead of Ethyl 3,5-dimethoxy-4-hydroxycinnamate and Methyl 1-bromo-2,3,4-triacetylglucuronate, the title compound (45) was obtained.

$^1$H-NMR (CDCl$_3$, δ-TMS) 7.54(d, 1H, J=15.6 Hz), 7.05 (s, 2H), 6.54(d, 1H, J=16.0 Hz), 6.16(d, 1H, J=1.2 Hz), 5.50~5.10(m, 3H), 4.78(s, 2H), 4.45~4.00(m, 3H), 3.78(s, 6H), 2.15(s, 3H), 2.11(s, 3H), 2.09(s, 3H), 2.05(s, 3H)

IR (KBr, cm$^{-1}$): 2850, 1740, 1250

Elemental analysis for: C$_{27}$H$_{31}$O$_{14}$Cl$_3$

Calculated (%): C, 47.28; H, 4.56; O, 32.66; Cl, 15.50.

Found (%): C, 47.30; H, 4.56; O, 32.70; Cl, 15.44.

EXAMPLE 58

3,5-dimethoxy-4-(tetra-O-acetyl-α-D-mannopyranosyloxy)cinnamic acid (compound 46)

In accordance with EXAMPLE 52, 1,1,1-Trichloroethyl 3,5-dimethoxy-4-(tetra-O-acetyl-α-D-mannopyranosyloxy) cinnamate was used instead of 1,1,1-Trichloroethyl 3,5-dimethoxy-4-(6-O-methyl-2,3,4-triacetyl-β-D-glcuropyranosyloxy cinnamate, the title compound (46) was obtained.

$^1$H-NMR (CDCl$_3$, δ-TMS) 12.28(bs, 1H), 7.54(d, 1H, J=15.6 Hz), 7.06(s, 2H), 6.54(d, 1H, J=16.0 Hz), 6.10(d, 1H, J=1.2 Hz), 5.50~5.10(m, 3H), 4.45~4.00(m, 3H), 3.79(s, 6H), 2.15(s, 3H), 2.11(s, 3H), 2.09(s, 3H), 2.05(s, 3H)

IR (KBr, cm$^{-1}$): 3340, 2850, 1740

Elemental analysis for: C$_{25}$H$_{30}$O$_{14}$

Calculated (%): C, 54.15; H, 5.46; O, 40.39.

Found (%): C, 54.08; H, 5.50; O, 40.42.

EXAMPLE 59

Benzyl 3,5-dimethoxy-4-(6-O-methyl-2,3,4-triacetyl-β-D-glcuropyranosyloxy)cinnamate (compound 47)

In accordance with EXAMPLE 41, benzyl 3,5-dimethoxy-4-hydroxycinnamate was used instead of Ethyl 3,5-dimethoxy-4-hydroxycinnamate, the title compound (47) was obtained.

$^1$H-NMR (CDCl$_3$, δ-TMS) 7.65~7.40(m, 5H), 7.10~6.80 (m, 3H), 6.73(s, 3H), 6.51(d, 1H, J=15.2 Hz), 5.84(d, 1H, J=7.2 Hz), 5.41~5.28(m, 3H), 4.21(t, 2H, J=7.2 Hz), 4.08(d, 1H, J=9.2 Hz), 3.78(s, 6H), 2.07(s, 3H), 2.04(s, 3H), 2.02(s, 3H)

IR (KBr, cm$^{-1}$): 2850, 1740, 1250

Elemental analysis for: C$_{31}$H$_{34}$O$_{14}$

Calculated (%): C, 59.05; H, 5.43; O, 35.52.

Found (%): C, 58.98; H, 5.41; O, 35.61.

Test Example 1

Acute toxicity test in mice

We performed this test in order to confirm the low toxicity of the compounds of the present invention, quinolinone derivatives. In the following, the method of the acute toxicity test will be explained.

Method: Each of quinolinone derivatives (compound No. 11~36) were forcibly administered orally at the doses of 2000 mg/kg to male ICR mice (body weight is 20~25 g, 5 mice per one(1) group), using an esophageal sound. After the administration, the animals were kept in cages for 7 days, to observed general symptoms and to count dead animals. Lethal dose (LD$_{50}$:mg/kg) was extrapolated from the mortality at 7th day after administration.

In result, the LD$_{50}$ of all compounds were over 2000 mg/kg, and therefore it was clearly shown that the compounds of the present invention, quinolinone derivatives, have extremely low toxicity.

Test Example 2

Effect on homologous passive cutaneous anaphylaxis (PCA) reaction in rats

We performed this pharmacological test by PCA reaction which was well known screening test for anti-allergic agents in order to demonstrate that the compounds of the present invention, glycosyloxyquinolinone derivatives, possess anti-allergic activity. This experimental animal model is caused by immediate type allergic reaction, namely, antigen-antibody reaction. In the following, the method of this pharmacological test will be explained.

Method: Male wistar rats (9 weeks old) were intradermally administered 0.05 ml of anti-serum against dinitrophenylated ascaris (DNP-As) into two sites on the shaved dorsal skin. 48 hours later, glycosyloxyquinolinone derivatives (test compounds) suspended in 0.5% methylcellulose (MC) were given i.v. at a dose of 0.5 mg/kg to the animals. 1 hour after administration of Test compounds, the animals were induced anaphylaxis by injection of saline (1 ml) dissolving 1 mg of trinitrophenylated ascaris (TNP-As) and 5 mg of Evans Blue into the tail vein of the animals. 30 minutes after induction of anaphylaxis, animals were anesthetized by ether and killed by bleeding, and were flayed dorsal skin. The leakage of dye was assessed by measuring the diameter (mean of shortest and longest diameter) of the blue spot on the inside surface of dorsal skin. As vehicle control group, only 0.5% MC solution was administered orally, and as positive control group, Tranilast suspended in 0.5% MC were administered orally at a dose of 100 mg/kg to the animals with the same method as the test compounds groups. The inhibition (%) of PCA reaction was calculated according to equation 1 and the result was shown in table 1. Each experimental group consisted of 5 rats.

In the conditions of this experiment, it was considered that the compound, which inhibited PCA reaction by over forty (40) percent against that in vehicle control group, was evidently effective for immediate type allergy.
(Equation 1)

$$\text{Inhibition (\%)}=(A-B)/A\times 100$$

In equation 1:
A: leakage of dye in vehicle control group
B: leakage of dye in test compound group or positive control group

TABLE 1

| compound No. | inhibition (%) |
|---|---|
| 14 | 54 |
| 15 | 42 |
| 16 | 41 |
| 20 | 49 |
| 21 | 46 |
| 22 | 42 |
| 26 | 50 |
| 27 | 46 |
| 28 | 43 |
| 32 | 45 |
| 33 | 40 |
| 34 | 42 |
| Tranilast | 52 |

As shown in table 1, the inhibition (%) of glycosyloxyquinolinone derivatives was 40 to 54 percent, it was demonstrated that glycosyloxyquinolinone derivatives have equivalent anti-allergic activity to Tranilast. The results of these examples clearly showed that the compounds of the present invention, glycosyloxyquinolinone derivatives, were useful anti-allergic agent for immediate type asthma, hay fever and atopic dermatitis etc.

Test Example 3

Effect on experimental immediate and delayed type asthma model in guinea pigs

The asthma is typical allergic disease and we carried out this pharmacological test by experimental asthmatic model in guinea pigs in order to confirm that the compounds of the present invention, compound 14, 16, 20, 26 and 32, suppress immediate and delayed type asthmatic response. In the following, the method of the pharmacological test will be explained.

Method: Male hartley guinea pigs were sensitized by exposured aerosolized ovalbumine (OVA) (1% in saline) for 10 minutes per a day at eight times. The aerosol was generated by an ultrasonic nebulizer (NE-U12, Omron inc.). One week after final sensitization, the animals were challenged with inhalation of OVA (2% in saline) for 5 minutes. The animals were pretreated with metyrapone (10 mg/kg, i.v.) at 1 and 4 hours before the challenge, and pyrilamine (10 mg/kg, i.p.) at 30 minutes before the challenge. airway resistance in the conscious animals were measured for 1 minute with PULMOS-1 (made in Medical Interface Project Station Inc.) at 1 minute, 2, 4, 5, 6, 7, 8 and 23 to 24 hours after the challenge. Compound 14, 16, 20, 26 and 32 (test compound) suspended in 0.5% methylcellulose (MC) solution were given i.v. at doses of 0.2 and 0.5 mg/kg 1 hour before and 3 hours after the challenge. As a positive control group, Prednisolone was given orally at a dose of 10 mg/kg 2 hours and 16 hours before the challenge. As vehicle control group, only 0.5% MC solution was given orally.

The evaluation of the effect of the compounds on immediate and delayed type asthmatic response was undertaken with percentage of change in airway resistance 1 minute after the challenge and the area under the response curve for percentage of change in airway resistance between 4 and 8 hours after the challenge, respectively.

The inhibition (%) of the compounds for immediate and delayed type asthmatic response was calculated according to equation 2 and the result was shown in table 2. Each experimental group consisted of 8 guinea pigs.
(equation 2)

$$\text{Inhibition (\%)}=(A-B)/A\times 100$$

In equation 2:
A: percentage of change in airway resistance in vehicle control group
B: percentage of change in airway resistance in test compound group or positive control group

TABLE 2

| compound No. | dose (mg/kg) | immediate type asthma inhibition % | delayed type asthma inhibition (%) |
|---|---|---|---|
| 14 | 0.2 | 29 | 64 |
| 14 | 0.5 | 37 | 73 |
| 16 | 0.2 | 22 | 42 |
| 16 | 0.5 | 26 | 51 |
| 20 | 0.2 | 27 | 57 |
| 20 | 0.5 | 38 | 61 |
| 26 | 0.2 | 25 | 52 |
| 26 | 0.5 | 37 | 63 |
| 32 | 0.2 | 26 | 49 |
| 32 | 0.5 | 34 | 57 |
| Prednisolone | 10 | 27 | 69 |

As shown in table 2, glycosyloxyquinolinone derivatives were equivalent or superior anti-asthmatic activity to Prednisolone. Therefore it is confirmed that glycosyloxyquinolinone derivatives have exceedingly high activity to inhibit against the immediate and delayed type asthma.

Formulation Example 1

(5% powders)

| the compound of the present invention | 50 mg |
|---|---|
| lactose | 950 mg |
| | 1000 mg |

In the following, the procedure for powders of compound 14 will be shown. Crystals of the compound of the present invention were pulverized in a mortar and thoroughly mixed with lactose. Secondly the mixture was pulverized with a pestle and 5% powders of compound 14 was obtained.

Formulation Example 2

(10% powders)

| the compound of the present invention | 100 mg |
|---|---|
| lactose | 900 mg |
| | 1000 mg |

In the following, the procedure for powders of compound 20 will be shown. The procedure of FORMULATION EXAMPLE 1 was repeated to obtain 10% powders of compound 20.

Formulation Example 3

(10% granules)

| the compound of the present invention | 300 mg |
|---|---|
| lactose | 2000 mg |
| starch | 670 mg |
| gelatin | 30 mg |
| | 3000 mg |

In the following, the procedure for granules of compound 14 will be shown. The compound of the present invention was mixed with the equivalent amount of starch and pulverized in a mortar. This was further mixed with lactose and the remaining portion of starch. Separately from this, 30 mg of gelatin was mixed with 1 ml of purified water, solubilized by heating, cooled and then, with stirring, mixed with 1 ml of ethanol to prepare a gelatin solution. Thereafter, the mixture prepared above was mixed with the gelatin solution, and the resulting mixture was kneaded, granulated and then dried to obtain granules of compound 14.

Formulation Example 4

(5 mg tablets)

| the compound of the present invention | 5 mg |
|---|---|
| lactose | 62 mg |
| starch | 30 mg |
| talc | 2 mg |
| magnesium stearate | 1 mg |
| | 100 mg/tablet |

In the following, the procedure for tablets of compound 14 will be shown. A 20 times larger portion of the above composition was used to prepare tablets each of which containing 5 mg of the active ingredient. That is, 100 mg of the compound of the present invention in a crystal form was pulverized in a mortar and mixed with lactose and starch. The thus prepared formulation was mixed with 10% starch paste, and the mixture was kneaded and then subjected to granulation. After drying, the resulting granules were mixed with talc and magnesium stearate and subjected to tablet making in usual way. With the above procedure, tablets of compound 14 was prepared.

Formulation Example 5

(20 mg tablets)

| the compound of the present invention | 20 mg |
|---|---|
| 6% hydroxypropylcellulose/lactose | 75 mg |
| stearate/talc | 2 mg |
| potato starch | 3 mg |
| | 100 mg/tablet |

In the following, the procedure for tablets of compound 20 will be shown. A 10 times larger portion of the above composition was used to prepare tablets each of which containing 20 mg of the active ingredient. That is, 6 g of hydroxypropylcellulose was dissolved in an appropriate volume of ethanol and mixed with 94 g of lactose, followed by kneading. After drying to a degree, the mixture was passed through a No. 60 mesh, and the thus graded granules were used as 6% hydroxypropylcellulose/lactose. Separately from this, magnesium stearate and talc were mixed at a ratio of 1:4 and used as stearate/talc. Thereafter, the compound of the present invention, 6% hydroxypropylcellulose/lactose, stearate/talc and potato starch were thoroughly mixed and subjected to tablet making in usual way. With the above procedure, tablets of compound 20 was prepared.

Formulation Example 6

(25 mg tablets)

| the compound of the present invention | 25 mg |
|---|---|
| lactose | 122 mg |
| carboxymethylstarch | 50 mg |
| talc | 2 mg |
| magnesium stearate | 1 mg |
| | 200 mg/tablet |

In the following, the procedures for tablets of compound 26 will be shown. A 10 times larger portion of the above composition was used to prepare tablets each of which containing 25 mg of the active ingredient. That is, 250 mg of the compound of the present invention in a crystal form was pulverized in a mortar and thoroughly mixed with lactose. An appropriate volume of purified water was added to carboxymethylstarch, which was subsequently added to the above mixture, and the resulting mixture was kneaded and then subjected to granulation. After drying, the thus prepared granules were mixed with talc and magnesium stearate and subjected to tablet making in usual way. With the above procedure, tablets of compound 26 was prepared.

Formulation Example 7

(100 mg capsules)

| the compound of the present invention | 300 mg |
|---|---|
| lactose | 2000 mg |
| starch | 670 mg |
| gelatin | 30 mg |
| | 3000 mg |

In the following, the procedures for tablets of compound 20 will be shown. Granules were prepared in accordance with the procedure described in Formulation EXAMPLE 3 and packed in capsules in 100 mg portions. With the above procedure, capsules of compound 20 was prepared.

Formulation Example 8

| (0.1% injections) | |
|---|---|
| the compound of the present invention | 5 mg |
| normal saline solution | balance |
| | 10 ml |

A 5 mg of sodium salt of compound 14 was dissolved in normal saline solution, total volume of the resulting solution was adjusted to 10 ml by gradually adding normal saline solution for injection use and then the thus prepared solution was sealed in an ampoule aseptically.

Thus, it is apparent that there has been provided, in accordance with the present invention, a novel glycosyloxyquinolinone derivative, which is effective as medicine, a simple method for preparing the same, the nitro glycosyloxyquinolinone derivatives, amino glycosyloxyquinolinone derivatives and sinapinic acid derivatives effective as an intermediate in said method. Also provided novel glycosyloxyquinolinone derivative and its physiologically acceptable salt are excellent antiallergic agents which have low toxicity and are useful for the treatment or prevention of immediate type and delayed type allergic diseases, particularly an excellent antiallergic agent which is highly effective on delayed type allergy that cannot be treated effectively with the prior art antiallergic agents.

While the invention has been described in detail and with reference to specific embodiments thereof, it will be apparent to one skilled in the art that various changes and modifications can be made therein without departing from the spirit and scope thereof.

What is claimed is:

1. A quinolinone glycoside or a physiologically acceptable salt thereof, expressed by formula (I):

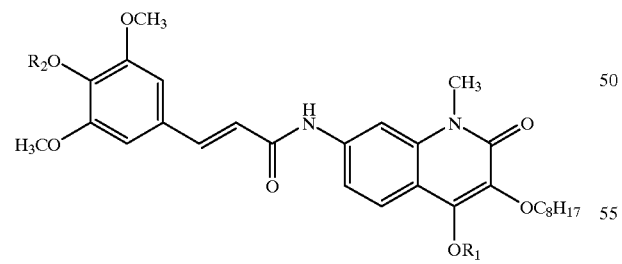

(I)

(wherein, each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which a hydroxyl group is unprotected or protected with an acyl group having a carbon number of 2 to 7 or a benzyl group).

2. A quinolinone glycoside or a physiologically acceptable salt thereof according to claim 1, wherein each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which no hydroxyl group is protected.

3. A quinolinone glycoside or a physiologically acceptable salt thereof according to claim 1, wherein each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which a hydroxyl group is protected with an acyl group having a carbon number of 2 to 7 or a benzyl group.

4. A quinolinone glycoside or a physiologically acceptable salt thereof according to claim 2, wherein each of $R_1$ and $R_2$ is a hydrogen atom or a glucuronyl group in which no hydroxyl group is protected.

5. A quinolinone glycoside or a physiologically acceptable salt thereof according to claim 2, wherein each of $R_1$ and $R_2$ is a hydrogen atom or a glucosyl group in which no hydroxyl group is protected.

6. A quinolinone glycoside or a physiologically acceptable salt thereof according to claim 2, wherein each of $R_1$ and $R_2$ is a hydrogen atom or a galactosyl group in which no hydroxyl group is protected.

7. A quinolinone glycoside or a physiologically acceptable salt thereof according to claim 2, wherein each of $R_1$ and $R_2$ is a hydrogen atom or a mannosyl group in which no hydroxyl group is protected.

8. A quinolinone glycoside or a physiologically acceptable salt thereof according to claim 4, wherein each of $R_1$ and $R_2$ is a glucuronyl group in which no hydroxyl group is protected.

9. A quinolinone glycoside or a physiologically acceptable salt thereof according to claim 4, wherein $R_1$ is a hydrogen atom, and $R_2$ is a glucuronyl group in which no hydroxyl group is protected.

10. A quinolinone glycoside or a physiologically acceptable salt thereof according to claim 4, wherein $R_1$ is a glucuronyl group in which no hydroxyl group is protected, and $R_2$ is a hydrogen atom.

11. A pharmaceutical composition comprising, as an active ingredient, a quinolinone glycoside or a physiologically acceptable salt thereof as in any one of claims 2 and 4 to 10 and a pharmaceutically acceptable carrier.

12. A quinolinone glycoside or a physiologically acceptable salt thereof, expressed by formula (II):

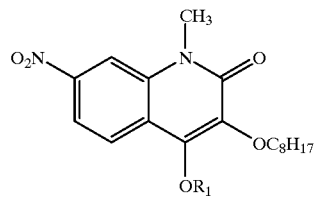

(II)

(wherein $R_1$ is a glycosyl group selected from the group consisting of a glucuronyl group, a glucosyl group, a galactosyl group and a mannosyl group, in which a hydroxyl group is unprotected or protected with an acyl group having a carbon number of 2 to 7 or a benzyl group).

13. A quinolinone glycoside or a physiologically acceptable salt thereof, expressed by formula (III):

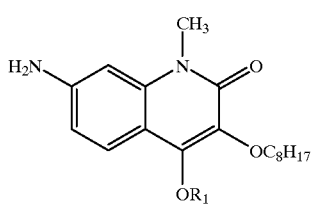

(III)

(wherein R₁ is a glycosyl group selected from the group consisting of a glucuronyl group, a glucosyl group, a galactosyl group and a mannosyl group, in which a hydroxyl group is unprotected or protected with an acyl group having a carbon number of 2 to 7 or a benzyl group).

14. A quinolinone glycoside or a physiologically acceptable salt thereof according to claim 12, wherein R₁ is a glucuronyl group in which a hydroxyl group is protected or unprotected.

15. A quinolinone glycoside or a physiologically acceptable salt thereof according to claim 13, wherein R₁ is a glucuronyl group in which a hydroxyl group is protected or unprotected.

16. A process for producing a quinolinone glycoside expressed by formula (II):

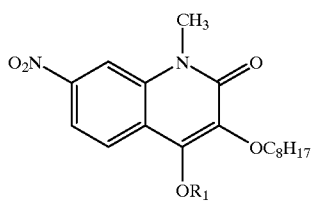

(II)

(wherein R₁ is a glycosyl group selected form the group consisting of a glucuronyl group, a glucosyl group, a galactosyl group and a mannosyl group, in which a hydroxyl group is unprotected or protected with an acyl group having a carbon number of 2 to 7 or a benzyl group), comprising the steps of:

reacting a quinolinone derivative expressed by formula (IV):

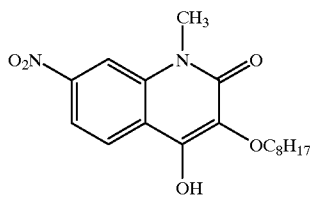

(IV)

with a basic substance; and
conducting a glycosylation reaction with a glycosyl-1-halide having a glycosyl moiety selected from the group consisting of glucuronic acid, glucose, galactose and mannose, wherein at least one hydroxyl of said glycosyl moiety is protected with an acyl group having a carbon number of 2 to 7 or a benzyl group.

17. A process for producing a quinolinone glycoside according to claim 16, wherein the basic substance is at least one selected from the group consisting of alkaline metal hydrides, alkaline earth metal hydrides and amines.

18. A process for producing a quinolinone glycoside expressed by formula (III):

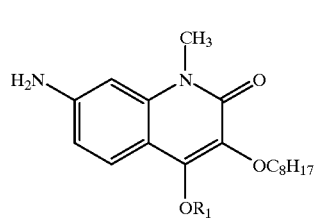

(III)

(wherein R₁ is a glycosyl group selected from the group consisting of a glucuronyl group, a glucosyl group, a galactosyl group and a mannosyl group, in which a hydroxyl group is unprotected or protected with an acyl group having a carbon number of 2 to 7 or a benzyl group), comprising the step of reducing a quinolinone glycoside expressed by formula (II):

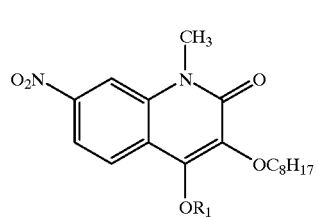

(II)

(wherein, in the formula, R₁ is a glycosyl group selected from the group consisting of a glucuronyl group, a glucosyl group, a galactosyl group and a mannosyl group, in which a hydroxyl group is unprotected or protected with an acyl group having a carbon number of 2 to 7 or a benzyl group), in the presence of hydrogen and/or a metallic catalyst.

19. A process for producing a quinolinone glycoside expressed by formula (I):

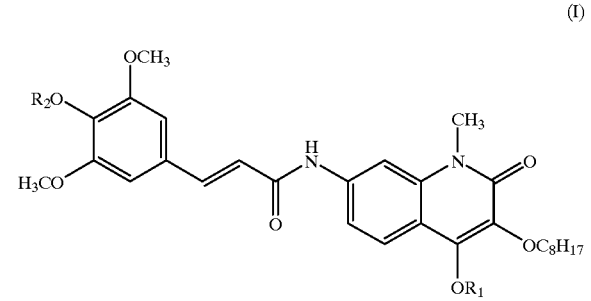

(I)

(wherein each of R₁ and R₂ is a hydrogen atom or a glycosyl group selected from the group consisting of a glucuronyl group, a glucosyl group, a galactosyl group and a mannosyl group, and at least one of R₁ and R₂ is a glycosyl group in which a hydroxyl group is unprotected or protected with an acyl group having a carbon number of 2 to 7 or a benzyl group), the process comprising the step of conducting amidation between a quinolinone glycoside expressed by formula (III):

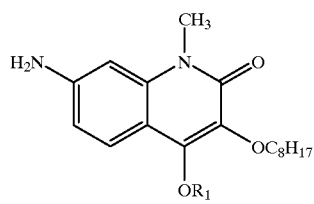

(III)

(wherein R₁ is a glycosyl group selected from the group consisting of a glucuronyl group, a glucosyl group, a galactosyl group and a mannosyl group, in which a hydroxyl group is unprotected or protected with an acyl group having a carbon number of 2 to 7 or a benzyl group), and a sinapic acid derivative expressed by formula (VII):

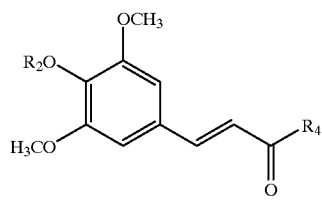

(VII)

(wherein $R_2$ is a hydrogen atom or a glycosyl group selected from the group consisting of a glucuronyl group, a glucosyl group, a galactosyl group and a mannosyl group, in which a hydroxyl group is protected or unprotected, and $R_4$ is a hydroxyl group or a halogen atom).

20. A process for producing a quinolinone glycoside expressed by formula (I):

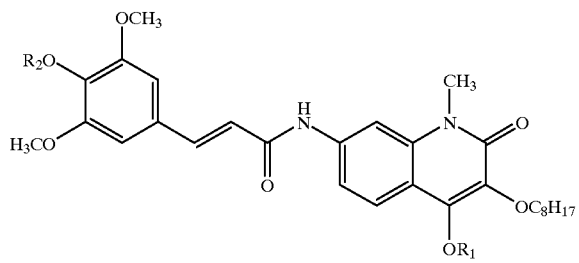

(I)

(wherein each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which a hydroxyl group is unprotected or protected with an acyl group having a carbon number of 2 to 7 or a benzyl group), comprising the steps of:

reacting a quinolinone derivative expressed by formula (VI):

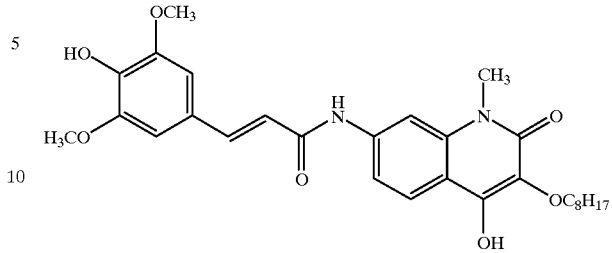

(VI)

with a basic substance; and then conducting a glycosylation reaction with a glycosyl halide, which is obtained by substituting a hydrogen atom at 1-position of a glycose, selected from the group consisting of glucuronic acid, glucose, galactose and mannose, by a halogen atom, and in which a hydroxyl group is protected with an acyl group having a carbon number of 2 to 7 or a benzyl group.

21. A process for producing a quinolinone glycoside expressed by formula (I) in which no hydroxyl group in the glycosyl group is protected, comprising the step of eliminating a protecting group in a glycosyl group in a quinolinone glycoside expressed by formula (I) in which a hydroxyl group in the glycosyl group is protected

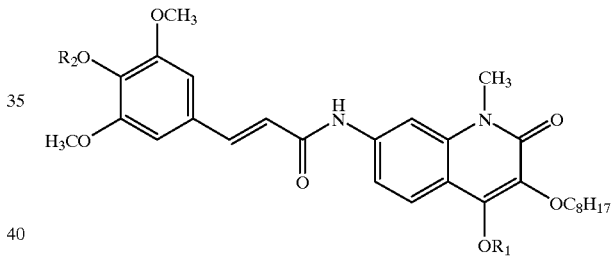

(I)

(wherein each of $R_1$ and $R_2$ is a hydrogen atom or a glycosyl group selected from the group consisting of a glucuronyl group, a glucosyl group, a galactosyl group and a mannosyl group, and at least one of $R_1$ and $R_2$ is a glycosyl group in which a hydroxyl group is unprotected or protected with an acyl group having a carbon number of 2 to 7 or a benzyl group).

22. A process for producing a sinapic acid glycoside expressed by formula (V):

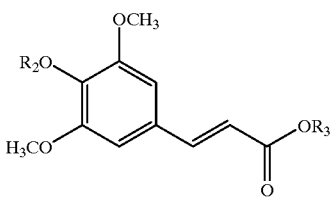

(V)

(wherein $R_2$ is a glycosyl group selected from the group consisting of a glucuronyl group, a glucosyl group, a galactosyl group and a mannosyl group, in which a hydroxyl group in the glycosyl group is unprotected or protected with an acyl group having a carbon number of 2 to 7 or a benzyl group, and R₃ is selected from the group consisting of a hydrogen atom, an alkyl group, an aryl group and an aralkyl group), comprising the steps of:

reacting a sinapic acid ester with a basic substance; and then conducting a glycosylation reaction with a glycosyl halide, which is obtained by substituting a hydrogen atom at 1-position of a hexose, selected from the group consisting of glucuronic acid, glucose, galactose and mannose, by a halogen atom, and in which a hydroxyl group is protected with an acyl group having a carbon number of 2 to 7 or a benzyl group.

23. A sinapic acid glycoside selected from the group consisting of 3,5-dimethoxy-4-(6-O-methyl-2,3,4-triacetyl-β-D-glucuropyranosyloxy)]cinnamic acid, Methyl[3,5-dimethoxy-4-(6-O-methyl-2,3,4-triacetyl-β-D-glucuropyranosyloxy)]cinnamate, Ethyl[3,5-dimethoxy-4-(6-O-methyl-2,3,4-triacetyl-β-D-glucuropyranosyloxy)cinnamate, 1,1,1-Trichloroethyl[3,5-dimethoxy-4-(6-O-methyl-2,3,4-triacetyl-β-D-glucuropyranosyloxy)]cinnamate, Phenyl[3,5-dimethoxy-4-(6-O-methyl-2,3,4-triacetyl-β-D-glucuropyranosyloxy)]cinnamate, Benzyl[3,5-dimethoxy-4-(6-O-methyl-2,3,4-triacetyl-β-D-glucuropyranosyloxy)]cinnamate, 3,5-dimethoxy-4-(tetra-O-acetyl-β-D-glucopyranosyloxy)cinnamic acid, Methyl[3,5-dimethoxy-4-(tetra-O-acetyl-β-D-glucopyranosyloxy)]cinnamate, 1,1,1-Trichloroethyl[3,5-dimethoxy-4-(tetra-O-acetyl-β-D-glucopyranosyloxy)]cinnamate, Phenyl[3,5-dimethoxy-4-(tetra-O-acetyl-β-D-glucopyranosyloxy)]cinnamate, Benzyl[3,5-dimethoxy-4-(tetra-O-acetyl-β-D-galactopyranosyloxy)]cinnamate, 3,5-dimethoxy-4-(tetra-O-acetyl-β-D-galactopyranosyloxy) cinnamic acid, Methyl[3,5-dimethoxy-4-(tetra-O-acetyl-β-D-galactopyranosyloxy)]cinnamate, Ethyl[3,5-dimethoxy-4-(tetra-O-acetyl-β-D-galactopyranosyloxy)]cinnamate, 1,1,1-Trichloroethyl[3,5-dimethoxy-4-(tetra-O-acetyl-β-D-galactopyranosyloxy)]cinnamate, Phenyl[3,5-dimethoxy-4-(tetra-O-acetyl-β-D-galactopyranosyloxy)]cinnamate, Benzyl[3,5-dimethoxy-4-(tetra-O-acetyl-β-D-galactopyranosyloxy)]cinnamate, 3,5-dimethoxy-4-(tetra-O-acetyl-α-D-mannopyranosyloxy) cinnamic acid, Methyl[3,5-dimethoxy-4-(tetra-O-acetyl-α-D-mannopyranosyloxy)]cinnamate, Ethyl[3,5-dimethoxy-4-(tetra-O-acetyl-α-D-mannopyranosyloxy)]cinnamate, 1,1,1-Trichloroethyl[3,5-dimethoxy-4-(tetra-O-acetyl-α-D-mannopyranosyloxy)]cinnamate, Phenyl[3,5-dimethoxy-4-(tetra-O-acetyl-α-D-mannopyranosyloxy)]cinnamate, Benzyl[3,5-dimethoxy-4-(tetra-O-acetyl-α-D-mannopyranosyloxy)]cinnamate, 3,5-dimethoxy-4-(6-O-methyl-2,3,4-tribenzoyl-β-D-glucuropyranosyloxy) cinnamic acid, Methyl[3,5-dimethoxy-4-(6-O-methyl-2,3,4-tribenzoyl-β-D-glucuropyranosyloxy)]cinnamate, Ethyl[3,5-dimethoxy-4-(6-O-methyl-2,3,4-tribenzoyl-β-D-glucuropyranosyloxy)]cinnamate, 1,1,1-Trichloroethyl[3,5-dimethoxy-4-(6-O-methyl-2,3,4-tribenzoyl-β-D-glucuropyranosyloxy)]cinnamate, 3,5-dimethoxy-4-(tetra-O-benzoyl-β-D-glucopyranosyloxy)cinnamic acid, Methyl[3,5-dimethoxy-4-(tetra-O-benzoyl-β-D-glucopyranosyloxy)]cinnamate, Ethyl[3,5-dimethoxy-4-(tetra-O-benzoyl-β-D-glucopyranosyloxy)] cinnamate, 1,1,1-Trichloroethyl[3,5-dimethoxy-4-(tetra-O-benzoyl-β-D-glucopyranosyloxy)]cinnamate, Phenyl[3,5-dimethoxy-4-(tetra-O-benzoyl-β-D-glucopyranosyloxy)]cinnamate, Benzyl[3,5-dimethoxy-4-(tetra-O-benzoyl-β-D-glucopyranosyloxy)]cinnamate, 3,5-dimethoxy-4-(tetra-O-benzoyl-β-D-galactopyranosyloxy) cinnamic acid, Methyl[3,5-dimethoxy-4-(tetra-O-benzoyl-β-D-galactopyranosyloxy]cinnamate, Ethyl[3,5-dimethoxy-4-(tetra-O-benzoyl-β-D-galactopyranosyloxy)] cinnamate, 1,1,1-Trichlorethyl[3,5-dimethoxy-4-(tetra-O-benzoyl-β-D-galactopyranosyloxy)]cinnamate, Phenyl[3,5-dimethoxy-4-(tetra-O-benzoyl-β-D-galactopyranosyloxy)]cinnamate, Benzyl[3,5-dimethoxy-4-(tetra-O-benzoyl-β-D-galactopyranosyloxy)]cinnamate, 3,5-dimethoxy-4-(tetra-O-benzoyl-α-D-mannopyranosyloxy)cinnamic acid, Methyl[3,5-dimethoxy-4-(tetra-O-benzoyl-α-D-mannopyranosyloxy)]cinnamate, Ethyl[3,5-dimethoxy-4-(tetra-O-benzoyl-α-D-mannopyranosyloxy)]cinnamate, 1,1,1-Trichloroethyl[3,5-dimethoxy-4-(tetra-O-benzoyl-α-D-mannopyranosyloxy)]cinnamate, Phenyl[3,5-dimethoxy-4-(tetra-O-benzoyl-α-D-mannopyranosyloxy)]cinnamate, Benzyl[3,5-dimethoxy-4-(tetra-O-benzoyl-α-D-mannopyranosyloxy)]cinnamate, 3,5-dimethoxy-4-(6-O-methyl-2,3,4-tribenzyl-β-D-glucuropyranosyloxy) cinnamic acid, Methyl[3,5-dimethoxy-4-(6-O-methyl-2,3,4-tribenzyl-β-D-glucuropyranosyloxy)]cinnamate, Ethyl[3,5-dimethoxy-4-(6-O-methyl-2,3,4-tribenzyl-β-D-glucuropyranosyloxy)]cinnamate, 1,1,1-Trichloroethyl[3,5-dimethoxy-4-(6-O-methyl-2,3,4-tribenzyl-β-D-glucuropyranosyloxy)]cinnamate, Phenyl[3,5-dimethoxy-4-(6-O-methyl-2,3,4-tribenzyl-β-D-glucuropyranosyloxy)]cinnamate, Benzyl[3,5-dimethoxy-4-(6-O-methyl-2,3,4-tribenzyl-β-D-glucuropyranosyloxy)]cinnamate, 3,5-dimethoxy-4-(tetra-O-benzyl-β-D-glucopyranosyloxy)cinnamic acid, Methyl[3,5-dimethoxy-4-(tetra-O-benzyl-β-D-glucopyranosyloxy)]cinnamate, Ethyl[3,5-dimethoxy-4-(tetra-O-β-D-glucopyranosyloxy)]cinnamate, 1,1,1-Trichloroethyl[3,5-dimethoxy-4-(tetra-O-benzyl-β-D-glucopyranosyloxy)]cinnamate, Phenyl[3,5-dimethoxy-4-(tetra-O-benzyl-β-D-glucopyranosyloxy)]cinnamate, Benzyl[3,5-dimethoxy-4-(tetra-O-benzyl-β-D-glucopyranosyloxy)]cinnamate, 3,5-dimethoxy-4-(tetra-O-benzyl-β-D-galactopyranosyloxy)cinnamic acid, Methyl[3,5-dimethoxy-4-(tetra-O-benzyl-β-D-galactopyranosyloxy)]cinnamate, Ethyl[3,5-dimethoxy-4-(tetra-O-benzyl-β-D-galactopyranosyloxy)]cinnamate, 1,1,1-Trichloroethyl[3,5-dimethoxy-4-(tetra-O-benzyl-β-D-galactopyranosyloxy)]cinnamate, Phenyl[3,5-dimethoxy-4-(tetra-O-benzyl-β-D-galactopyranosyloxy)]cinnamate, Benzyl[3,5-dimethoxy-4-(tetra-O-benzyl-β-D-galactopyranosyloxy)]cinnamate, 3,5-dimethoxy-4-(tetra-O-benzyl-α-D-mannopyranosyloxy)cinnamic acid, Methyl[3,5-dimethoxy-4-(tetra-O-benzyl-α-D-mannopyranosyloxy)]cinnamate, Ethyl[3,5-dimethoxy-4-(tetra-O-benzyl-α-D-mannopyranosyloxy)]cinnamate, 1,1,1-Trichloroethyl[3,5-dimethoxy-4-(tetra-O-benzyl-α-D-mannopyranosyloxy)]cinnamate. Phenyl[3,5- dimethoxy-4-(tetra-O-benzyl-α-D-mannopyranosyloxy)]cinnamate, Benzyl[3,5-dimethoxy-4-(tetra-O-benzyl-α-D-mannopyranosyloxy)]cinnamate, 3,5-dimethoxy-4-(β-D-glucuropyranosyloxy) cinnamic acid, Methyl[3,5-dimethoxy-4-(β-D-glucuropyranosyloxy)]cinnamate, Ethyl[3,5-dimethoxy-4-(β-D-glucuropyranosyloxy)]cinnamate, 1,1,1-Trichloroethyl[3,5-dimethoxy-4-(β-D-glucuropyranosyloxy)]cinnamate, Phenyl[3,5-dimethoxy-4-(β-D-glucuropyaanosyloxy)]cinnamate, Benzyl[3,5-dimethoxy-4-(β-D-glucuropyranosyloxy)]cinnamate, 3,5-dimethoxy-4-(β-D-glucopyranosyloxy) cinnamic acid, Methyl[3,5-dimethoxy-4-(β-D-glucopyranosyloxy)]cinnamate, Ethyl[3,5-dimethoxy-4-(β-D-glucopyranosyloxy)]cinnamate, 1,1,1-Trichloroethyl[3,5-dimethoxy-4-(β-D-glucopyranosyloxy)]cinnamate, Phenyl[3,5-dimethoxy-4-(β-D-glucopyranosyloxy)]cinnamate, Benzyl[3,5-dimethoxy-4-(β-D-glucopyranosyloxy)]cinnamate, 3,5-dimethoxy-4-(β-D-galactopyranosyloxy) cinnamic acid, Methyl[3,5-dimethoxy-4-(β-D-galactopyranosyloxy)]cinnamate, Ethyl[3,5-dimethoxy-4-(β-D-galactopyranosyloxy)]cinnamate, 1,1,1-Trichloroethyl[3,5-dimethoxy-4-(β-D-galactopyranosyloxy)]cinnamate, Phenyl[3,5-dimethoxy-4-(β-D-galactopyranosyloxy)]cinnamate, Benzyl[3,5-dimethoxy-4-(β-D-galactopyranosyloxy)]cinnamate, 3,5-dimethoxy-4-(α-D-mannopyranosyloxy) cinnamic acid, Methyl[3,5-dimethoxy-4-(α-D-mannopyranosyloxy)]cinnamate, Ethyl[3,5-dimethoxy-4-(α-D-mannopyranosyloxy)]cinnamate 1,1,1-Trichloroethyl[3,5-dimethoxy-4-(α-D-mannopyranosyloxy)]cinnamate, Phenyl[3,5-dimethoxy-4-(α-D-mannopyranosyloxy)]cinnamate, Benzyl[3,5-dimethoxy-4-(α-D-mannopyranosyloxy)]cinnamate, and physiologically acceptable salts of these compounds.

24. A method of treating an allergic disease of a mammal, the method comprising administering a pathologically effective amount of a quinolinone glycoside or a physiologically acceptable salt thereof as in any one of claims 2 and 4 to 10.

* * * * *